United States Patent
Yasuoka et al.

(10) Patent No.: US 11,753,449 B2
(45) Date of Patent: *Sep. 12, 2023

(54) IMMUNOGLOBULIN BINDING PROTEIN, AND AFFINITY SUPPORT USING SAME

(71) Applicants: JSR CORPORATION, Minato-ku (JP); JSR Life Sciences Corporation, Minato-ku (JP); JSR Life Sciences, LLC, Sunnyvale, CA (US); JSR Micro N. V., Leuven (BE)

(72) Inventors: Jun-ichi Yasuoka, Minato-ku (JP); Kiichi Yoshimura, Minato-ku (JP)

(73) Assignees: JSR CORPORATION, Minato-ku (JP); JSR Life Sciences Corporation, Minato-ku (JP); JSR Life Sciences, LLC, Sunnyvale, CA (US); JSR Micro N.V., Leuven (BE)

( * ) Notice: Subject to any disclaimer, the term of this patent is extended or adjusted under 35 U.S.C. 154(b) by 579 days.

This patent is subject to a terminal disclaimer.

(21) Appl. No.: 16/649,879

(22) PCT Filed: Sep. 25, 2018

(86) PCT No.: PCT/JP2018/035418
§ 371 (c)(1),
(2) Date: Mar. 23, 2020

(87) PCT Pub. No.: WO2019/059399
PCT Pub. Date: Mar. 28, 2019

(65) Prior Publication Data
US 2021/0163545 A1  Jun. 3, 2021

(30) Foreign Application Priority Data

Sep. 25, 2017 (JP) ................. 2017-184158

(51) Int. Cl.
*C07K 14/195* (2006.01)
*C07K 1/22* (2006.01)
*C07K 14/00* (2006.01)
*C12P 21/02* (2006.01)

(52) U.S. Cl.
CPC .............. *C07K 14/195* (2013.01); *C07K 1/22* (2013.01); *C07K 14/001* (2013.01); *C12P 21/02* (2013.01)

(58) Field of Classification Search
CPC ................. C07K 14/70503; C07K 14/195
See application file for complete search history.

(56) References Cited

U.S. PATENT DOCUMENTS

| | | | |
|---|---|---|---|
| 6,884,629 | B2 | 4/2005 | Gore et al. |
| 2005/0100970 | A1 | 5/2005 | Uhlen et al. |
| 2010/0286373 | A1 | 11/2010 | Majima et al. |
| 2017/0327545 | A1 | 11/2017 | Rodrigo et al. |
| 2018/0016306 | A1 | 1/2018 | Yoshida |
| 2018/0305414 | A1 | 10/2018 | Majima et al. |
| 2019/0119333 | A1 | 4/2019 | Yoshida |
| 2020/0262873 | A1 | 8/2020 | Yasuoka et al. |

FOREIGN PATENT DOCUMENTS

| | | | |
|---|---|---|---|
| JP | 2016-79149 A | 5/2016 | |
| WO | WO 00/23580 A1 | 4/2000 | |
| WO | WO 2005/033130 A2 | 4/2005 | |
| WO | WO-2005033130 A2 * | 4/2005 | ........... C07K 14/315 |
| WO | WO 2007/097361 A1 | 8/2007 | |
| WO | WO 2016/096643 A1 | 6/2016 | |
| WO | WO 2016/121703 A1 | 8/2016 | |
| WO | WO-2016121703 A1 * | 8/2016 | ............... C07K 1/22 |
| WO | WO 2017/069158 A1 | 4/2017 | |
| WO | WO 2017/191748 A1 | 11/2017 | |
| WO | WO 2019/059400 A1 | 3/2019 | |

OTHER PUBLICATIONS

GenCore sequence alignment, obtained Jul. 15, 2022, 4 pages (Year: 2022).*
Robert Andrew Phillips ,Modified Immunoglobulin-Binding Domains of Protein L From Peptostreptococcua Magnus, University of Southampton, 2006 (Year: 2006).*
Murphy et al., "Nucleotide sequence of the gene for peptostreptococcal protein L", DNA Sequence—J.DNA Sequencing and Mapping , 1994, 259-265 (Year: 1994).*
Finegoldia magna protein L gene, complete cds Gen Bank: L04466.1 (Year: 2007).*
International Search Report dated Dec. 11, 2018 in PCT/JP2018/035418 filed on Sep. 25, 2018, 2 pages.
Svensson et al., "Contributions of Amino Acid Side Chains to the Kinetics and Thermodynamics of the Bivalent Binding of Protein L to Ig k Light Chain", Biochemistry, 2004, vol. 43, No. 9, pp. 2445-2457.
Japanese Office Action dated Sep. 13, 2022 in Japanese Patent Application No. 2019-543140 (with unedited computer generated English translation), 6 pages.

* cited by examiner

Primary Examiner — Lianko G Garyu
(74) Attorney, Agent, or Firm — Oblon, McClelland, Maier & Neustadt, L.L.P.

(57) ABSTRACT

Provided are a protein L-derived immunoglobulin binding protein having an increased alkali tolerance, and an affinity support using the same. Disclosed are an immunoglobulin binding protein comprising at least one mutant of an immunoglobulin binding domain, and an affinity support comprising a solid-phase support having the immunoglobulin binding protein bound thereto. A mutant of the immunoglobulin binding domain consists of an amino acid sequence having an identity of at least 85% with the sequence set forth in any one of SEQ ID NO:1 to SEQ ID NO:9 and a predetermined mutation, and the mutant has immunoglobulin κ chain binding activity.

13 Claims, No Drawings
Specification includes a Sequence Listing.

SEQUENCE LISTING

```
<160> NUMBER OF SEQ ID NOS: 23

<210> SEQ ID NO 1
<211> LENGTH: 76
<212> TYPE: PRT
<213> ORGANISM: Finegoldia magna
<220> FEATURE:
<223> OTHER INFORMATION: Protein L, B1 domain

<400> SEQUENCE: 1

Lys Glu Glu Thr Pro Glu Thr Pro Glu Thr Asp Ser Glu Glu Val
1               5                   10                  15

Thr Ile Lys Ala Asn Leu Ile Phe Ala Asn Gly Ser Thr Gln Thr Ala
            20                  25                  30

Glu Phe Lys Gly Thr Phe Glu Lys Ala Thr Ser Glu Ala Tyr Ala Tyr
        35                  40                  45

Ala Asp Thr Leu Lys Lys Asp Asn Gly Glu Tyr Thr Val Asp Val Ala
    50                  55                  60

Asp Lys Gly Tyr Thr Leu Asn Ile Lys Phe Ala Gly
65                  70                  75

<210> SEQ ID NO 2
<211> LENGTH: 72
<212> TYPE: PRT
<213> ORGANISM: Finegoldia magna
<220> FEATURE:
<223> OTHER INFORMATION: Protein L, B2 domain

<400> SEQUENCE: 2

Lys Glu Lys Thr Pro Glu Glu Pro Lys Glu Glu Val Thr Ile Lys Ala
1               5                   10                  15

Asn Leu Ile Tyr Ala Asp Gly Lys Thr Gln Thr Ala Glu Phe Lys Gly
            20                  25                  30

Thr Phe Glu Glu Ala Thr Ala Glu Ala Tyr Arg Tyr Ala Asp Ala Leu
        35                  40                  45

Lys Lys Asp Asn Gly Glu Tyr Thr Val Asp Val Ala Asp Lys Gly Tyr
    50                  55                  60

Thr Leu Asn Ile Lys Phe Ala Gly
65                  70

<210> SEQ ID NO 3
<211> LENGTH: 72
<212> TYPE: PRT
<213> ORGANISM: Finegoldia magna
<220> FEATURE:
<223> OTHER INFORMATION: Protein L, B3 domain
```

<400> SEQUENCE: 3

Lys Glu Lys Thr Pro Glu Glu Pro Lys Glu Glu Val Thr Ile Lys Ala
1               5                   10                  15

Asn Leu Ile Tyr Ala Asp Gly Lys Thr Gln Thr Ala Glu Phe Lys Gly
            20                  25                  30

Thr Phe Glu Glu Ala Thr Ala Glu Ala Tyr Arg Tyr Ala Asp Leu Leu
        35                  40                  45

Ala Lys Glu Asn Gly Lys Tyr Thr Val Asp Val Ala Asp Lys Gly Tyr
    50                  55                  60

Thr Leu Asn Ile Lys Phe Ala Gly
65                  70

<210> SEQ ID NO 4
<211> LENGTH: 72
<212> TYPE: PRT
<213> ORGANISM: Finegoldia magna
<220> FEATURE:
<223> OTHER INFORMATION: Protein L, B4 domain

<400> SEQUENCE: 4

Lys Glu Lys Thr Pro Glu Glu Pro Lys Glu Glu Val Thr Ile Lys Ala
1               5                   10                  15

Asn Leu Ile Tyr Ala Asp Gly Lys Thr Gln Thr Ala Glu Phe Lys Gly
            20                  25                  30

Thr Phe Ala Glu Ala Thr Ala Glu Ala Tyr Arg Tyr Ala Asp Leu Leu
        35                  40                  45

Ala Lys Glu Asn Gly Lys Tyr Thr Ala Asp Leu Glu Asp Gly Gly Tyr
    50                  55                  60

Thr Ile Asn Ile Arg Phe Ala Gly
65                  70

<210> SEQ ID NO 5
<211> LENGTH: 73
<212> TYPE: PRT
<213> ORGANISM: Finegoldia magna
<220> FEATURE:
<223> OTHER INFORMATION: Protein L, B5 domain

<400> SEQUENCE: 5

Lys Lys Val Asp Glu Lys Pro Glu Glu Lys Glu Gln Val Thr Ile Lys
1               5                   10                  15

Glu Asn Ile Tyr Tyr Glu Asp Gly Thr Val Gln Thr Ala Thr Phe Lys
            20                  25                  30

Gly Thr Phe Ala Glu Ala Thr Ala Glu Ala Tyr Arg Tyr Ala Asp Leu
        35                  40                  45

Leu Ser Lys Glu His Gly Lys Tyr Thr Ala Asp Leu Glu Asp Gly Gly
    50                  55                  60

Tyr Thr Ile Asn Ile Arg Phe Ala Gly
65                  70

<210> SEQ ID NO 6
<211> LENGTH: 72
<212> TYPE: PRT
<213> ORGANISM: Finegoldia magna
<220> FEATURE:
<223> OTHER INFORMATION: Protein L, C1 domain

```
<400> SEQUENCE: 6

Lys Glu Thr Pro Glu Pro Glu Lys Glu Val Thr Ile Lys Ala Asn
1               5                   10                  15

Leu Ile Phe Ala Asp Gly Ser Thr Gln Asn Ala Thr Phe Lys Gly Thr
            20                  25                  30

Phe Ala Lys Ala Val Ser Asp Ala Tyr Ala Tyr Ala Asp Ala Leu Lys
            35                  40                  45

Lys Asp Asn Gly Glu Tyr Thr Val Asp Val Ala Asp Lys Gly Leu Thr
        50                  55                  60

Leu Asn Ile Lys Phe Ala Gly Lys
65                  70

<210> SEQ ID NO 7
<211> LENGTH: 71
<212> TYPE: PRT
<213> ORGANISM: Finegoldia magna
<220> FEATURE:
<223> OTHER INFORMATION: Protein L, C2 domain

<400> SEQUENCE: 7

Lys Glu Lys Pro Glu Glu Pro Lys Glu Glu Val Thr Ile Lys Val Asn
1               5                   10                  15

Leu Ile Phe Ala Asp Gly Lys Thr Gln Thr Ala Thr Phe Lys Gly Thr
            20                  25                  30

Phe Glu Glu Ala Thr Ala Lys Ala Tyr Ala Tyr Ala Asp Leu Leu Ala
            35                  40                  45

Lys Glu Asn Gly Glu Tyr Thr Ala Asp Leu Glu Asp Gly Gly Asn Thr
        50                  55                  60

Ile Asn Ile Lys Phe Ala Gly
65                  70

<210> SEQ ID NO 8
<211> LENGTH: 74
<212> TYPE: PRT
<213> ORGANISM: Finegoldia magna
<220> FEATURE:
<223> OTHER INFORMATION: Protein L, C3 domain

<400> SEQUENCE: 8

Lys Glu Thr Pro Glu Thr Pro Glu Glu Pro Lys Glu Glu Val Thr Ile
1               5                   10                  15

Lys Val Asn Leu Ile Phe Ala Asp Gly Lys Ile Gln Thr Ala Thr Phe
            20                  25                  30

Lys Gly Thr Phe Glu Glu Ala Thr Ala Lys Ala Tyr Ala Tyr Ala Asn
            35                  40                  45

Leu Leu Ala Lys Glu Asn Gly Glu Tyr Thr Ala Asp Leu Glu Asp Gly
        50                  55                  60

Gly Asn Thr Ile Asn Ile Lys Phe Ala Gly
65                  70

<210> SEQ ID NO 9
<211> LENGTH: 75
<212> TYPE: PRT
<213> ORGANISM: Finegoldia magna
<220> FEATURE:
<223> OTHER INFORMATION: Protein L, C4 domain
```

<400> SEQUENCE: 9

Lys Glu Thr Pro Glu Thr Pro Glu Glu Pro Lys Glu Val Thr Ile
1               5                   10                  15

Lys Val Asn Leu Ile Phe Ala Asp Gly Lys Thr Gln Thr Ala Thr Phe
            20                  25                  30

Lys Gly Thr Phe Glu Glu Ala Thr Ala Glu Ala Tyr Arg Tyr Ala Asp
        35                  40                  45

Leu Leu Ala Lys Val Asn Gly Glu Tyr Thr Ala Asp Leu Glu Asp Gly
    50                  55                  60

Gly Tyr Thr Ile Asn Ile Lys Phe Ala Gly Lys
65                  70                  75

<210> SEQ ID NO 10
<211> LENGTH: 75
<212> TYPE: PRT
<213> ORGANISM: Finegoldia magna
<220> FEATURE:
<223> OTHER INFORMATION: KBP1

<400> SEQUENCE: 10

Lys Glu Thr Pro Glu Thr Pro Glu Glu Pro Lys Glu Val Thr Ile
1               5                   10                  15

Arg Val Asn Leu Ile Phe Ala Asp Gly Lys Thr Gln Thr Ala Thr Phe
            20                  25                  30

Lys Gly Thr Phe Glu Glu Ala Thr Ala Glu Ala Tyr Arg Tyr Ala Asp
        35                  40                  45

Leu Leu Ala Lys Val Asn Gly Glu Tyr Thr Ala Asp Leu Glu Asp Gly
    50                  55                  60

Gly Tyr Thr Ile Asn Ile Lys Phe Ala Gly Lys
65                  70                  75

<210> SEQ ID NO 11
<211> LENGTH: 75
<212> TYPE: PRT
<213> ORGANISM: Finegoldia magna
<220> FEATURE:
<223> OTHER INFORMATION: KBP2

<400> SEQUENCE: 11

Lys Glu Thr Pro Glu Thr Pro Glu Glu Pro Lys Glu Val Thr Ile
1               5                   10                  15

Lys Val Asn Leu Ile Phe Ala Asp Gly Arg Thr Gln Thr Ala Thr Phe
            20                  25                  30

Lys Gly Thr Phe Glu Glu Ala Thr Ala Glu Ala Tyr Arg Tyr Ala Asp
        35                  40                  45

Leu Leu Ala Lys Val Asn Gly Glu Tyr Thr Ala Asp Leu Glu Asp Gly
    50                  55                  60

Gly Tyr Thr Ile Asn Ile Lys Phe Ala Gly Lys
65                  70                  75

<210> SEQ ID NO 12
<211> LENGTH: 75
<212> TYPE: PRT
<213> ORGANISM: Finegoldia magna
<220> FEATURE:
<223> OTHER INFORMATION: KBP3

<400> SEQUENCE: 12

Lys Glu Thr Pro Glu Thr Pro Glu Pro Lys Glu Val Thr Ile
1               5                   10                  15

Lys Val Asn Leu Ile Phe Ala Asp Gly Lys Thr Gln Thr Ala Thr Phe
                20                  25                  30

Lys Gly Arg Phe Glu Glu Ala Thr Ala Glu Ala Tyr Arg Tyr Ala Asp
            35                  40                  45

Leu Leu Ala Lys Val Asn Gly Glu Tyr Thr Ala Asp Leu Glu Asp Gly
        50                  55                  60

Gly Tyr Thr Ile Asn Ile Lys Phe Ala Gly Lys
65                  70                  75

<210> SEQ ID NO 13
<211> LENGTH: 75
<212> TYPE: PRT
<213> ORGANISM: Finegoldia magna
<220> FEATURE:
<223> OTHER INFORMATION: KBP4

<400> SEQUENCE: 13

Lys Glu Thr Pro Glu Thr Pro Glu Pro Lys Glu Val Thr Ile
1               5                   10                  15

Lys Val Asn Leu Ile Phe Ala Asp Gly Lys Thr Gln Thr Ala Thr Phe
                20                  25                  30

Lys Gly Thr Phe Glu Glu Ala Thr Ala Glu Ala Phe Arg Tyr Ala Asp
            35                  40                  45

Leu Leu Ala Lys Val Asn Gly Glu Tyr Thr Ala Asp Leu Glu Asp Gly
        50                  55                  60

Gly Tyr Thr Ile Asn Ile Lys Phe Ala Gly Lys
65                  70                  75

<210> SEQ ID NO 14
<211> LENGTH: 75
<212> TYPE: PRT
<213> ORGANISM: Finegoldia magna
<220> FEATURE:
<223> OTHER INFORMATION: KBP5

<400> SEQUENCE: 14

Lys Glu Thr Pro Glu Thr Pro Glu Pro Lys Glu Val Thr Ile
1               5                   10                  15

Lys Val Asn Leu Ile Phe Ala Asp Gly Lys Thr Gln Thr Ala Thr Phe
                20                  25                  30

Lys Gly Thr Phe Glu Glu Ala Thr Ala Glu Ala Tyr Arg Tyr Ala Asp
            35                  40                  45

Leu Leu Ala Lys Val Gln Gly Glu Tyr Thr Ala Asp Leu Glu Asp Gly
        50                  55                  60

Gly Tyr Thr Ile Asn Ile Lys Phe Ala Gly Lys
65                  70                  75

<210> SEQ ID NO 15
<211> LENGTH: 76
<212> TYPE: PRT
<213> ORGANISM: Finegoldia magna
<220> FEATURE:
<223> OTHER INFORMATION: KBP6

-continued

```
<400> SEQUENCE: 15

Lys Glu Thr Pro Glu Thr Pro Glu Pro Lys Glu Val Thr Ile
1               5                   10                  15

Lys Val Asn Leu Ile Phe Ala Asp Gly Lys Thr Gln Thr Ala Thr Phe
            20                  25                  30

Lys Gly Thr Phe Glu Glu Ala Thr Ala Glu Ala Tyr Arg Tyr Ala Asp
        35                  40                  45

Leu Leu Ala Lys Val Asn Ala Gly Glu Tyr Thr Ala Asp Leu Glu Asp
    50                  55                  60

Gly Gly Tyr Thr Ile Asn Ile Lys Phe Ala Gly Lys
65                  70                  75

<210> SEQ ID NO 16
<211> LENGTH: 76
<212> TYPE: PRT
<213> ORGANISM: Finegoldia magna
<220> FEATURE:
<223> OTHER INFORMATION: KBP7

<400> SEQUENCE: 16

Lys Glu Thr Pro Glu Thr Pro Glu Pro Lys Glu Val Thr Ile
1               5                   10                  15

Lys Val Asn Leu Ile Phe Ala Asp Gly Lys Thr Gln Thr Ala Thr Phe
            20                  25                  30

Lys Gly Thr Phe Glu Glu Ala Thr Ala Glu Ala Tyr Arg Tyr Ala Asp
        35                  40                  45

Leu Leu Ala Lys Val Asn Tyr Gly Glu Tyr Thr Ala Asp Leu Glu Asp
    50                  55                  60

Gly Gly Tyr Thr Ile Asn Ile Lys Phe Ala Gly Lys
65                  70                  75

<210> SEQ ID NO 17
<211> LENGTH: 74
<212> TYPE: PRT
<213> ORGANISM: Finegoldia magna
<220> FEATURE:
<223> OTHER INFORMATION: KBP8

<400> SEQUENCE: 17

Lys Glu Thr Glu Thr Pro Glu Glu Pro Lys Glu Val Thr Ile Lys
1               5                   10                  15

Val Asn Leu Ile Phe Ala Asp Gly Lys Thr Gln Thr Ala Thr Phe Lys
            20                  25                  30

Gly Thr Phe Glu Glu Ala Thr Ala Glu Ala Tyr Arg Tyr Ala Asp Leu
        35                  40                  45

Leu Ala Lys Val Asn Gly Glu Tyr Thr Ala Asp Leu Glu Asp Gly Gly
    50                  55                  60

Tyr Thr Ile Asn Ile Lys Phe Ala Gly Lys
65                  70

<210> SEQ ID NO 18
<211> LENGTH: 73
<212> TYPE: PRT
<213> ORGANISM: Finegoldia magna
<220> FEATURE:
<223> OTHER INFORMATION: KBP9
```

```
<400> SEQUENCE: 18

Lys Glu Thr Glu Thr Glu Glu Pro Lys Glu Glu Val Thr Ile Lys Val
1               5                   10                  15

Asn Leu Ile Phe Ala Asp Gly Lys Thr Gln Thr Ala Thr Phe Lys Gly
            20                  25                  30

Thr Phe Glu Glu Ala Thr Ala Glu Ala Tyr Arg Tyr Ala Asp Leu Leu
        35                  40                  45

Ala Lys Val Asn Gly Glu Tyr Thr Ala Asp Leu Glu Asp Gly Gly Tyr
    50                  55                  60

Thr Ile Asn Ile Lys Phe Ala Gly Lys
65                  70

<210> SEQ ID NO 19
<211> LENGTH: 72
<212> TYPE: PRT
<213> ORGANISM: Finegoldia magna
<220> FEATURE:
<223> OTHER INFORMATION: KBP10

<400> SEQUENCE: 19

Lys Glu Thr Glu Thr Glu Glu Lys Glu Glu Val Thr Ile Lys Val Asn
1               5                   10                  15

Leu Ile Phe Ala Asp Gly Lys Thr Gln Thr Ala Thr Phe Lys Gly Thr
            20                  25                  30

Phe Glu Glu Ala Thr Ala Glu Ala Tyr Arg Tyr Ala Asp Leu Leu Ala
        35                  40                  45

Lys Val Asn Gly Glu Tyr Thr Ala Asp Leu Glu Asp Gly Gly Tyr Thr
    50                  55                  60

Ile Asn Ile Lys Phe Ala Gly Lys
65                  70

<210> SEQ ID NO 20
<211> LENGTH: 75
<212> TYPE: PRT
<213> ORGANISM: Finegoldia magna
<220> FEATURE:
<223> OTHER INFORMATION: KBP11

<400> SEQUENCE: 20

Lys Glu Thr Pro Glu Thr Pro Glu Glu Pro Lys Glu Glu Val Thr Ile
1               5                   10                  15

Arg Val Asn Leu Ile Phe Ala Asp Gly Arg Thr Gln Thr Ala Thr Phe
            20                  25                  30

Lys Gly Thr Phe Glu Glu Ala Thr Ala Glu Ala Tyr Arg Tyr Ala Asp
        35                  40                  45

Leu Leu Ala Lys Val Asn Gly Glu Tyr Thr Ala Asp Leu Glu Asp Gly
    50                  55                  60

Gly Tyr Thr Ile Asn Ile Lys Phe Ala Gly Lys
65                  70                  75

<210> SEQ ID NO 21
<211> LENGTH: 75
<212> TYPE: PRT
<213> ORGANISM: Finegoldia magna
<220> FEATURE:
<223> OTHER INFORMATION: KBP12
```

```
<400> SEQUENCE: 21

Lys Glu Thr Pro Glu Thr Pro Glu Glu Pro Lys Glu Glu Val Thr Ile
1               5                   10                  15

Lys Val Asn Leu Ile Phe Ala Asp Gly Arg Thr Gln Thr Ala Thr Phe
            20                  25                  30

Lys Gly Arg Phe Glu Glu Ala Thr Ala Glu Ala Tyr Arg Tyr Ala Asp
        35                  40                  45

Leu Leu Ala Lys Val Gln Gly Glu Tyr Thr Ala Asp Leu Glu Asp Gly
        50                  55                  60

Gly Tyr Thr Ile Asn Ile Lys Phe Ala Gly Lys
65                  70                  75

<210> SEQ ID NO 22
<211> LENGTH: 75
<212> TYPE: PRT
<213> ORGANISM: Finegoldia magna
<220> FEATURE:
<223> OTHER INFORMATION: KBP13

<400> SEQUENCE: 22

Lys Glu Thr Pro Glu Thr Pro Glu Glu Pro Lys Glu Glu Val Thr Ile
1               5                   10                  15

Lys Val Asn Leu Ile Phe Ala Asp Gly Arg Thr Gln Thr Ala Thr Phe
            20                  25                  30

Lys Gly Arg Phe Glu Glu Ala Thr Ala Lys Ala Tyr Arg Tyr Ala Asp
        35                  40                  45

Leu Leu Ala Lys Val Gln Gly Glu Tyr Thr Ala Asp Leu Glu Asp Gly
        50                  55                  60

Gly Tyr Thr Ile Asn Ile Lys Phe Ala Gly Lys
65                  70                  75

<210> SEQ ID NO 23
<211> LENGTH: 72
<212> TYPE: PRT
<213> ORGANISM: Finegoldia magna
<220> FEATURE:
<223> OTHER INFORMATION: KBP14

<400> SEQUENCE: 23

Lys Glu Thr Glu Thr Glu Glu Lys Glu Glu Val Thr Ile Arg Val Asn
1               5                   10                  15

Leu Ile Phe Ala Asp Gly Arg Thr Gln Thr Ala Thr Phe Lys Gly Arg
            20                  25                  30

Phe Glu Glu Ala Thr Ala Lys Ala Tyr Arg Tyr Ala Asp Leu Leu Ala
        35                  40                  45

Lys Val Gln Gly Glu Tyr Thr Ala Asp Leu Glu Asp Gly Gly Tyr Thr
        50                  55                  60

Ile Asn Ile Lys Phe Ala Gly Lys
65                  70
```

IMMUNOGLOBULIN BINDING PROTEIN, AND AFFINITY SUPPORT USING SAME

FIELD OF THE INVENTION

The present invention relates to an immunoglobulin binding protein, an affinity support using the same, and a method for isolating an antibody or a fragment thereof using the affinity support.

BACKGROUND OF THE INVENTION

In recent years, antibodies have been widely utilized in, for example, reagents for research and antibody drugs. These antibodies for reagents or drugs are generally purified by affinity chromatography. For affinity purification of an antibody, generally, columns to which a ligand which is a substance specifically binding with an immunoglobulin is immobilized are used. Generally, immunoglobulin binding proteins such as protein A, protein G, and protein L are used as such a ligand.

In general, an alkaline solution is used for washing the column for affinity purification, however, the immunoglobulin binding protein used for affinity ligand has low alkali tolerance. Therefore, improvement of alkali tolerance of the ligand protein is expected. Protein A is a ligand protein that has been relatively conventionally used for a relatively long time, and the technologies for enhancing the alkali tolerance have also been conventionally studied. For example, methods for improving alkali tolerance of protein A by, for example, modification of particular amino acids in C domain or Z domain (Patent Literature 1), or substitution of Asn residue (Patent Literature 2) are disclosed.

Since protein L binds with the immunoglobulin light chain κ domain, protein L is used for the purification of low-molecular weight antibodies such as Fab and a single-chain antibody (scFv). There are only few reports for protein L that has been modified for the use as an affinity ligand. For example, in Patent Literatures 3 and 4, immunoglobulin κ chain binding polypeptides containing a domain of protein L or a mutant thereof are described. In Examples of Patent Literature 5, an immunoglobulin κ chain variable region-binding peptide comprising an amino acid sequence in which one or more amino acid residues selected from the 15th-position, 16th-position, 17th-position, and 18th-position of the amino acid sequence of an immunoglobulin light chain κ domain-binding peptide of B5 domain of protein L have been substituted, and the acid dissociation pH is shifted toward the neutrality side compared to the value before the introduction of substitution, is described. Patent Literature 6 describes that an immunoglobulin binding domain comprising an amino acid sequence in which at least two or more sites selected from the group consisting of the 7th-position, 13th-position, 22th-position, and 29th-position of the amino acid sequence of an immunoglobulin binding domain of protein L have been substituted with a basic amino acid except for lysine or with an amino acid having a hydroxyl group, has excellent alkali stability.

CITATION LIST

Patent Literatures

Patent Literature 1: WO 2007/097361 A
Patent Literature 2: WO 2000/023580 A
Patent Literature 3: WO 2016/096643 A
Patent Literature 4: U.S. Pat. No. 6,884,629
Patent Literature 5: WO 2016/121703 A
Patent Literature 6: WO 2017/069158 A

SUMMARY OF THE INVENTION

Problems to be Solved by the Invention

Accordingly, a protein L-derived immunoglobulin binding domain having improved alkali tolerance for use as an affinity ligand is required. The present invention provides an immunoglobulin binding protein comprising a mutant of a protein L-derived immunoglobulin binding domain having improved alkali tolerance, and an affinity support using the same.

Means for Solving the Problem

The present invention provides the following:

An immunoglobulin binding protein,
comprising at least one mutant of an immunoglobulin binding domain,
wherein the mutant of the immunoglobulin binding domain consists of an amino acid sequence having an identity of at least 85% with the sequence set forth in any one of SEQ ID NO:1 to SEQ ID NO:9, the amino acid sequence having at least one mutation selected from the group consisting of the following (a) to (h), and the mutant has immunoglobulin κ chain binding activity:

(a) substitution with another amino acid residue or deletion of an amino acid residue at a position corresponding to the 17th-position of the amino acid sequence set forth in SEQ ID NO:9, or insertion of an amino acid residue into a position in front of or behind the relevant position;

(b) substitution with another amino acid residue or deletion of an amino acid residue at a position corresponding to the 26th-position of the amino acid sequence set forth in SEQ ID NO:9, or insertion of an amino acid residue into a position in front of or behind the relevant position;

(c) substitution with another amino acid residue or deletion of an amino acid residue at a position corresponding to the 35th-position of the amino acid sequence set forth in SEQ ID NO:9, or insertion of an amino acid residue into a position in front of or behind the relevant position;

(d) substitution with another amino acid residue or deletion of an amino acid residue at a position corresponding to the 42th-position of the amino acid sequence set forth in SEQ ID NO:9, or insertion of an amino acid residue into a position in front of or behind the relevant position;

(e) substitution with another amino acid residue or deletion of an amino acid residue at a position corresponding to the 44th-position of the amino acid sequence set forth in SEQ ID NO:9, or insertion of an amino acid residue into a position in front of or behind the relevant position;

(f) substitution with another amino acid residue or deletion of an amino acid residue at a position corresponding to the 54th-position of the amino acid sequence set forth in SEQ ID NO:9, or insertion of an amino acid residue into a position in front of or behind the relevant position;

(g) insertion of at least one amino acid residue between a position corresponding to the 54th-position and a position corresponding to the 55th-position of the amino acid sequence set forth in SEQ ID NO:9; and (h) deletion of at least one proline.

The present invention also provides a polynucleotide encoding the immunoglobulin binding protein.

The present invention also provides a vector comprising the polynucleotide.

The present invention also provides a transformant comprising the vector.

The present invention also provides an affinity support comprising a solid-phase support; and the immunoglobulin binding protein bound to the solid-phase support.

The present invention also provides a method for isolating an antibody or a fragment thereof, the method comprising using the affinity support.

The present invention also provides a method for producing an immunoglobulin binding protein, the method comprising expressing the immunoglobulin binding protein in the transformant or a cell-free protein synthesis system, or chemically synthesizing the immunoglobulin binding protein.

The present invention also provides the following:

A method for producing a mutant of an immunoglobulin binding domain, the method comprising introducing at least one mutation selected from the group consisting of the following (a) to (h) to a polypeptide consisting of an amino acid sequence set forth in any one of SEQ ID NO:1 to SEQ ID NO:9 or an amino acid sequence having an identity of at least 85% therewith, and having immunoglobulin κ chain binding activity:

(a) substitution with another amino acid residue or deletion of an amino acid residue at a position corresponding to the 17th-position of the amino acid sequence set forth in SEQ ID NO:9, or insertion of an amino acid residue into a position in front of or behind the relevant position;

(b) substitution with another amino acid residue or deletion of an amino acid residue at a position corresponding to the 26th-position of the amino acid sequence set forth in SEQ ID NO:9, or insertion of an amino acid residue into a position in front of or behind the relevant position;

(c) substitution with another amino acid residue or deletion of an amino acid residue at a position corresponding to the 35th-position of the amino acid sequence set forth in SEQ ID NO:9, or insertion of an amino acid residue into a position in front of or behind the relevant position;

(d) substitution with another amino acid residue or deletion of an amino acid residue at a position corresponding to the 42th-position of the amino acid sequence set forth in SEQ ID NO:9, or insertion of an amino acid residue into a position in front of or behind the relevant position;

(e) substitution with another amino acid residue or deletion of an amino acid residue at a position corresponding to the 44th-position of the amino acid sequence set forth in SEQ ID NO:9, or insertion of an amino acid residue into a position in front of or behind the relevant position;

(f) substitution with another amino acid residue or deletion of an amino acid residue at a position corresponding to the 54th-position of the amino acid sequence set forth in SEQ ID NO:9, or insertion of an amino acid residue into a position in front of or behind the relevant position;

(g) insertion of at least one amino acid residue between a position corresponding to the 54th-position and a position corresponding to the 55th-position of the amino acid sequence set forth in SEQ ID NO:9; and (h) deletion of at least one proline.

The present invention also provides a method for producing an affinity support, the method comprising immobilizing the immunoglobulin binding protein to a solid-phase support.

Effects of the Invention

The immunoglobulin binding protein of the present invention has high binding activity to the immunoglobulin κ chain and superior alkali tolerance, and therefore, the immunoglobulin binding protein is useful as an affinity ligand.

DETAILED DESCRIPTION OF THE INVENTION

Exemplary embodiments of the present invention will be described below.

[1] An immunoglobulin binding protein, comprising at least one mutant of an immunoglobulin binding domain, wherein the mutant of the immunoglobulin binding domain consists of an amino acid sequence having an identity of at least 85% with the sequence set forth in any one of SEQ ID NO:1 to SEQ ID NO:9, the amino acid sequence having at least one mutation selected from the group consisting of the following (a) to (h), and the mutant has immunoglobulin κ chain binding activity:

(a) substitution with another amino acid residue or deletion of an amino acid residue at a position corresponding to the 17th-position of the amino acid sequence set forth in SEQ ID NO:9, or insertion of an amino acid residue into a position in front of or behind the relevant position;

(b) substitution with another amino acid residue or deletion of an amino acid residue at a position corresponding to the 26th-position of the amino acid sequence set forth in SEQ ID NO:9, or insertion of an amino acid residue into a position in front of or behind the relevant position;

(c) substitution with another amino acid residue or deletion of an amino acid residue at a position corresponding to the 35th-position of the amino acid sequence set forth in SEQ ID NO:9, or insertion of an amino acid residue into a position in front of or behind the relevant position;

(d) substitution with another amino acid residue or deletion of an amino acid residue at a position corresponding to the 42th-position of the amino acid sequence set forth in SEQ ID NO:9, or insertion of an amino acid residue into a position in front of or behind the relevant position;

(e) substitution with another amino acid residue or deletion of an amino acid residue at a position corresponding to the 44th-position of the amino acid sequence set forth in SEQ ID NO:9, or insertion of an amino acid residue into a position in front of or behind the relevant position;

(f) substitution with another amino acid residue or deletion of an amino acid residue at a position corresponding to the 54th-position of the amino acid sequence set forth in SEQ ID NO:9, or insertion of an amino acid residue into a position in front of or behind the relevant position;

(g) insertion of at least one amino acid residue between a position corresponding to the 54th-position and a position corresponding to the 55th-position of the amino acid sequence set forth in SEQ ID NO:9; and (h) deletion of at least one proline.

[2] The immunoglobulin binding protein as described in [1], wherein the mutation of the (a) is substitution of an amino acid residue at a position corresponding to the 17th-position of the amino acid sequence set forth in SEQ ID NO:9 with another amino acid residue;

the mutation of the (b) is substitution of an amino acid residue at a position corresponding to the 26th-position of the amino acid sequence set forth in SEQ ID NO:9 with another amino acid residue;

the mutation of the (c) is substitution of an amino acid residue at a position corresponding to the 35th-position of the amino acid sequence set forth in SEQ ID NO:9 with another amino acid residue;

the mutation of the (d) is substitution of an amino acid residue at a position corresponding to the 42th-position of the amino acid sequence set forth in SEQ ID NO:9 with another amino acid residue;

the mutation of the (e) is substitution of an amino acid residue at a position corresponding to the 44th-position of the amino acid sequence set forth in SEQ ID NO:9 with another amino acid residue;

the mutation of the (f) is substitution of an amino acid residue at a position corresponding to the 54th-position of the amino acid sequence set forth in SEQ ID NO:9 with another amino acid residue;

the mutation of the (g) is insertion of an amino acid residue between a position corresponding to the 54th-position and a position corresponding to the 55th-position of the amino acid sequence set forth in SEQ ID NO:9; and the mutation of the (h) is deletion of one to three prolines.

[3] The immunoglobulin binding protein as described in [1] or [2], wherein the mutation of the (a) is substitution of lysine at a position corresponding to the 17th-position of the amino acid sequence set forth in SEQ ID NO:9 with arginine, glutamic acid, or aspartic acid;

the mutation of the (b) is substitution of lysine at a position corresponding to the 26th-position of the amino acid sequence set forth in SEQ ID NO:9 with arginine, glutamic acid, or aspartic acid;

the mutation of the (c) is substitution of threonine at a position corresponding to the 35th-position of the amino acid sequence set forth in SEQ ID NO:9 with arginine, glutamic acid, or aspartic acid;

the mutation of the (d) is substitution of glutamic acid at a position corresponding to the 42th-position of the amino acid sequence set forth in SEQ ID NO:9 with lysine;

the mutation of the (e) is substitution of tyrosine at a position corresponding to the 44th-position of the amino acid sequence set forth in SEQ ID NO:9 with phenylalanine or tryptophan;

the mutation of the (f) is substitution of asparagine at a position corresponding to the 54th-position of the amino acid sequence set forth in SEQ ID NO:9 with glutamine;

the mutation of the (g) is insertion of alanine, leucine, or tyrosine between asparagine at a position corresponding to the 54th-position and glycine at a position corresponding to the 55th-position of the amino acid sequence set forth in SEQ ID NO:9; and the mutation of the (h) is deletion of one or more prolines selected from the group consisting of proline at a position corresponding to the 4th-position, proline at a position corresponding to the 7th-position, and proline at a position corresponding to the 10th-position of the amino acid sequence set forth in SEQ ID NO:9.

[4] The immunoglobulin binding protein as described in any one of [1] to [3], wherein the mutant of the immunoglobulin binding domain consists of an amino acid sequence having an identity of at least 85% with the sequence set forth in any one of SEQ ID NO:1 to SEQ ID NO:9 and having at least one of the following (a') to (h'):

(a') arginine, glutamic acid, or aspartic acid at a position corresponding to the 17th-position of the amino acid sequence set forth in SEQ ID NO:9;

(b') arginine, glutamic acid, or aspartic acid at a position corresponding to the 26th-position of the amino acid sequence set forth in SEQ ID NO:9;

(c') arginine, glutamic acid, or aspartic acid at a position corresponding to the 35th-position of the amino acid sequence set forth in SEQ ID NO:9;

(d') lysine at a position corresponding to the 42th-position of the amino acid sequence set forth in SEQ ID NO:9;

(e') phenylalanine or tryptophan at a position corresponding to the 44th-position of the amino acid sequence set forth in SEQ ID NO:9;

(f') glutamine at a position corresponding to the 54th-position of the amino acid sequence set forth in SEQ ID NO:9;

(g') alanine, leucine, or tyrosine between a position corresponding to the 54th-position and a position corresponding to the 55th-position of the amino acid sequence set forth in SEQ ID NO:9; and (h') deletion of proline at at least one position selected from the group consisting of a position corresponding to the 4th-position, a position corresponding to the 7th-position, and a position corresponding to the 10th-position of the amino acid sequence set forth in SEQ ID NO:9.

[5] The immunoglobulin binding protein as described in any one of [1] to [4], wherein the mutant of the immunoglobulin binding domain consists of an amino acid sequence having an identity of at least 85% with the sequence set forth in any one of SEQ ID NO:1 to SEQ ID NO:9 and having any one of the following (a") to (l"):

(a") arginine at a position corresponding to the 17th-position of the amino acid sequence set forth in SEQ ID NO:9;

(b") arginine at a position corresponding to the 26th-position of the amino acid sequence set forth in SEQ ID NO:9;

(c") arginine at a position corresponding to the 35th-position of the amino acid sequence set forth in SEQ ID NO:9;

(d") lysine at a position corresponding to the 42th-position of the amino acid sequence set forth in SEQ ID NO:9;

(e") phenylalanine at a position corresponding to the 44th-position of the amino acid sequence set forth in SEQ ID NO:9;

(f") glutamine at a position corresponding to the 54th-position of the amino acid sequence set forth in SEQ ID NO:9;

($g_1$") alanine between a position corresponding to the 55th-position and a position corresponding to the 56th-position of the amino acid sequence set forth in SEQ ID NO:9;

($g_2$") tyrosine between a position corresponding to the 55th-position and a position corresponding to the 56th-position of the amino acid sequence set forth in SEQ ID NO:9;

($h_1$") deletion of proline at a position corresponding to the 4th-position of the amino acid sequence set forth in SEQ ID NO:9;

($h_2$") deletion of prolines at a position corresponding to the 4th-position and a position corresponding to the 7th-position of the amino acid sequence set forth in SEQ ID NO:9;

($h_3$") deletion of prolines at a position corresponding to the 4th-position, a position corresponding to the 7th-position, and a position corresponding to the 10th-position of the amino acid sequence set forth in SEQ ID NO:9;

(i") a combination of the (a") and (b");
(j") a combination of the (b"), (c"), and (f");
(k") a combination of the (b"), (c"), (d"), and (f"); and
(l") a combination of the (a"), (b"), (c"), (d"), (f"), and ($h_3$").

[6] The immunoglobulin binding protein as described in any one of [1] to [5], wherein the amino acid sequence set forth in any one of SEQ ID NO:1 to SEQ ID NO:9 is an amino acid sequence set forth in SEQ ID NO:9.

[7] The immunoglobulin binding protein as described in any one of [1] to [6], wherein the identity of at least 85% is an identity of at least 90%.

[8] The immunoglobulin binding protein as described in any one of [1] to [7], comprising two or more mutants of the immunoglobulin binding domain.

[9] A polynucleotide encoding the immunoglobulin binding protein as described in any one of [1] to [8].

[10] A vector comprising the polynucleotide as described in [9].

[11] A transformant comprising the vector as described in [10].

[12] An affinity support, comprising a solid-phase support; and the immunoglobulin binding protein as described in any one of [1] to [8] bound to the solid-phase support.

[13] A method for isolating an antibody or a fragment thereof, the method comprising using the affinity support as described in [12].

[14] A method for producing an immunoglobulin binding protein, the method comprising expressing the immunoglobulin binding protein as described in any one of [1] to [8] in the transformant as described in [11] or a cell-free protein synthesis system, or chemically synthesizing the immunoglobulin binding protein.

[15] A method for producing a mutant of an immunoglobulin binding domain, the method comprising introducing at least one mutation selected from the group consisting of the following (a) to (h) to a polypeptide consisting of an amino acid sequence set forth in any one of SEQ ID NO:1 to SEQ ID NO:9 or an amino acid sequence having an identity of at least 85% therewith, the polypeptide having immunoglobulin κ chain binding activity:

(a) substitution with another amino acid residue or deletion of an amino acid residue at a position corresponding to the 17th-position of the amino acid sequence set forth in SEQ ID NO:9, or insertion of an amino acid residue into a position in front of or behind the relevant position;

(b) substitution with another amino acid residue or deletion of an amino acid residue at a position corresponding to the 26th-position of the amino acid sequence set forth in SEQ ID NO:9, or insertion of an amino acid residue into a position in front of or behind the relevant position;

(c) substitution with another amino acid residue or deletion of an amino acid residue at a position corresponding to the 35th-position of the amino acid sequence set forth in SEQ ID NO:9, or insertion of an amino acid residue into a position in front of or behind the relevant position;

(d) substitution with another amino acid residue or deletion of an amino acid residue at a position corresponding to the 42th-position of the amino acid sequence set forth in SEQ ID NO:9, or insertion of an amino acid residue into a position in front of or behind the relevant position;

(e) substitution with another amino acid residue or deletion of an amino acid residue at a position corresponding to the 44th-position of the amino acid sequence set forth in SEQ ID NO:9, or insertion of an amino acid residue into a position in front of or behind the relevant position;

(f) substitution with another amino acid residue or deletion of an amino acid residue at a position corresponding to the 54th-position of the amino acid sequence set forth in SEQ ID NO:9, or insertion of an amino acid residue into a position in front of or behind the relevant position;

(g) insertion of at least one amino acid residue between a position corresponding to the 54th-position and a position corresponding to the 55th-position of the amino acid sequence set forth in SEQ ID NO:9; and (h) deletion of at least one proline.

[16] The production method as described in [15], wherein the mutation of the (a) is substitution of the amino acid residue at a position corresponding to the 17th-position of the amino acid sequence set forth in SEQ ID NO:9 with another amino acid residue;

the mutation of the (b) is substitution of the amino acid residue at a position corresponding to the 26th-position of the amino acid sequence set forth in SEQ ID NO:9 with another amino acid residue;

the mutation of the (c) is substitution of the amino acid residue at a position corresponding to the 35th-position of the amino acid sequence set forth in SEQ ID NO:9 with another amino acid residue;

the mutation of the (d) is substitution of the amino acid residue at a position corresponding to the 42th-position of the amino acid sequence set forth in SEQ ID NO:9 with another amino acid residue;

the mutation of the (e) is substitution of the amino acid residue at a position corresponding to the 44th-position of the amino acid sequence set forth in SEQ ID NO:9 with another amino acid residue;

the mutation of the (f) is substitution of the amino acid residue at a position corresponding to the 54th-position of the amino acid sequence set forth in SEQ ID NO:9 with another amino acid residue;

the mutation of the (g) is insertion of an amino acid residue between a position corresponding to the 54th-position and a position corresponding to the 55th-position of the amino acid sequence set forth in SEQ ID NO:9; and the mutation of the (h) is deletion of one to three prolines.

[17] The production method as described in [15] or [16], wherein the mutation of the (a) is substitution of lysine at a position corresponding to the 17th-position of the amino acid sequence set forth in SEQ ID NO:9 with arginine, glutamic acid, or aspartic acid;

the mutation of the (b) is substitution of lysine at a position corresponding to the 26th-position of the amino acid sequence set forth in SEQ ID NO:9 with arginine, glutamic acid, or aspartic acid;

the mutation of the (c) is substitution of threonine at a position corresponding to the 35th-position of the amino acid sequence set forth in SEQ ID NO:9 with arginine, glutamic acid, or aspartic acid;

the mutation of the (d) is substitution of glutamic acid at a position corresponding to the 42th-position of the amino acid sequence set forth in SEQ ID NO:9 with lysine;

the mutation of the (e) is substitution of tyrosine at a position corresponding to the 44th-position of the amino acid sequence set forth in SEQ ID NO:9 with phenylalanine or tryptophan;

the mutation of the (f) is substitution of asparagine at a position corresponding to the 54th-position of the amino acid sequence set forth in SEQ ID NO:9 with glutamine;

the mutation of the (g) is insertion of alanine, leucine, or tyrosine between asparagine at a position corresponding to the 54th-position and glycine at a position corresponding to the 55th-position of the amino acid sequence set forth in SEQ ID NO:9; and the mutation of the (h) is deletion of one or more prolines selected from the group consisting of proline at a position corresponding to the 4th-position, proline at a position corresponding to the 7th-position, and proline at a position corresponding to the 10th-position of the amino acid sequence set forth in SEQ ID NO:9.

[18] The production method as described in any one of [15] to [17], wherein
the at least one mutation is any one of the following (a") to (l"):
(a") substitution of lysine at a position corresponding to the 17th-position of the amino acid sequence set forth in SEQ ID NO:9 with arginine;
(b") substitution of lysine at a position corresponding to the 26th-position of the amino acid sequence set forth in SEQ ID NO:9 with arginine;
(c") substitution of threonine at a position corresponding to the 35th-position of the amino acid sequence set forth in SEQ ID NO:9 with arginine;
(d") substitution of glutamic acid at a position corresponding to the 42th-position of the amino acid sequence set forth in SEQ ID NO:9 with lysine;
(e") substitution of tyrosine at a position corresponding to the 44th-position of the amino acid sequence set forth in SEQ ID NO:9 with phenylalanine;
(f") substitution of asparagine at a position corresponding to the 54th-position of the amino acid sequence set forth in SEQ ID NO:9 with glutamine;
($g_1$") insertion of alanine between a position corresponding to the 54th-position and a position corresponding to the 55th-position of the amino acid sequence set forth in SEQ ID NO:9;
($g_2$") insertion of tyrosine between a position corresponding to the 54th-position and a position corresponding to the 55th-position of the amino acid sequence set forth in SEQ ID NO:9;
($h_1$") deletion of proline at a position corresponding to the 4th-position of the amino acid sequence set forth in SEQ ID NO:9;
($h_2$") deletion of prolines at a position corresponding to the 4th-position and a position corresponding to the 7th-position of the amino acid sequence set forth in SEQ ID NO:9;
($h_3$") deletion of prolines at a position corresponding to the 4th-position, a position corresponding to the 7th-position, and a position corresponding to the 10th-position of the amino acid sequence set forth in SEQ ID NO:9;
(i") a combination of the (a") and (b");
(j") a combination of the (b"), (c"), and (f");
(k") a combination of the (b"), (c"), (d"), and (f"); and
(l") a combination of the (a"), (b"), (c"), (d"), (f"), and ($h_3$").
[19] The production method as described in any one of [15] to [18], wherein the amino acid sequence set forth in any one of SEQ ID NO:1 to SEQ ID NO:9 is an amino acid sequence set forth in SEQ ID NO:9.
[20] The production method as described in any one of [15] to [19], wherein the identity of at least 85% is an identity of at least 90%.
[21] The production method as described in any one of [15] to [20], wherein the mutant of the immunoglobulin binding domain has enhanced alkali tolerance compared to the parent domain.
[22] The production method as described in any one of [15] to [21], the method further comprising expressing the polypeptide having the mutation applied thereto in the transformant as described in [11] or a cell-free protein synthesis system, or chemically synthesizing the polypeptide.
[23] A method for producing an affinity support, the method comprising immobilizing the immunoglobulin binding protein as described in any one of [1] to [8] on a solid-phase support.

According to the present specification, the identity of amino acid sequences or nucleotide sequences can be determined by using the algorithm BLAST (Pro. Natl. Acad. Sci. USA, 1993, 90:5873-5877) proposed by Karlin and Altschul. Based on this BLAST algorithm, programs called BLASTN, BLASTX, BLASTP, TBLASTN, and TBLASTX have been developed (J. Mol. Biol., 1990, 215:403-410). In a case in which these programs are used, the default parameters of the respective programs are used. Specific techniques of these analysis methods are known (see www.ncbi.nlm.nih.gov).

According to the present specification, the "identity of at least 85%" related to amino acid sequences and nucleotide sequences means an identity of 85% or higher, preferably an identity of 90% or higher, more preferably an identity of 95% or higher, even more preferably an identity of 97% or higher, still more preferably an identity of 98% or higher, and even more preferably an identity of 99% or higher. Furthermore, the "identity of at least 90%" related to amino acid sequences and nucleotide sequences means an identity of 90% or higher, preferably an identity of 95% or higher, more preferably an identity of 97% or higher, even more preferably an identity of 98% or higher, and still more preferably an identity of 99% or higher.

According to the present specification, a "corresponding position" on an amino acid sequence and a nucleotide sequence can be determined by subjecting a target sequence and a reference sequence (for example, an amino acid sequence set forth in SEQ ID NO:9) to alignment so as to give the maximum homology to a conserved amino acid residue or nucleotide present in each amino acid sequence or nucleotide sequence. The alignment can be carried out using a known algorithm, and the procedure thereof is known to those ordinarily skilled in the art. For example, the alignment can be carried out using Clustal W Multiple Alignment Programs (Thompson, J. D. et al., 1994, Nucleic Acids Res., 22:4673-4680) with default settings. Clustal W can be utilized, for example, from the websites of European Bioinformatics Institute: EBI [www.ebi.ac.uk/index.html]) or the DNA Data Bank of Japan (DDBJ [www.ddbj.nig.ac.jp/Welcome-j.html]) operated by the National Institute of Genetics.

According to the present specification, amino acid residues may also be described by the following abbreviations: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), valine (Val or V); and an arbitrary amino acid residue (Xaa or X). Furthermore, according to the present specification, the amino acid sequence of a peptide is described according to a conventional method such that the amino terminal (hereinafter, referred to as N-terminal) is positioned on the left-hand side, and the carboxyl terminal (hereinafter, referred to as C-terminal) is positioned on the right-hand side.

According to the present specification, the positions "in front of" and "behind" with respect to a particular position of an amino acid sequence refer to the positions N-terminally adjacent and C-terminally adjacent to the particular position, respectively. For example, in a case in which amino acid residues are inserted into the positions "in front of" and "behind" a particular position, the amino acid residues after insertion is disposed at positions N-terminally adjacent and C-terminally adjacent to the particular position.

According to the present specification, protein L refers to protein L, which is one type of proteins produced by Finegoldia magna.

According to the present specification, the term "immunoglobulin binding protein" refers to a protein having binding activity to an immunoglobulin (or an antibody or a fragment of an antibody). According to the present specification, the term "immunoglobulin" (Ig) includes immunoglobulins of any arbitrary classes, such as IgG, IgA, IgD, IgE, IgM, and subclasses of these. The term "antibody" according to the present specification refers to an immunoglobulin or a fragment thereof comprising an antigen recognition site, and examples can include immunoglobulins of any arbitrary classes such as IgG, IgA, IgD, IgE, IgM, and subclasses of these; fragments thereof; and mutants of the immunoglobulins and the fragments. Furthermore, the "antibody" according to the present specification may also be, for example, a chimeric antibody such as a humanized antibody, an antibody complex, or another immunoglobulin modification product comprising an antigen recognition site. Furthermore, the "fragment of an antibody" according to the present specification may be a fragment of an antibody comprising an antigen recognition site, or a fragment of an antibody that does not comprise an antigen recognition site. Examples of the fragment of an antibody that does not comprise an antigen recognition site comprise a protein comprising the Fc region only of an immunoglobulin, an Fc fusion protein, and mutants and modification products thereof.

According to the present specification, the term "immunoglobulin binding domain" refers to a functional unit of a polypeptide having immunoglobulin (or an antibody or a fragment of an antibody) binding activity by itself, the functional unit being contained in an immunoglobulin binding protein. Examples of this "immunoglobulin binding domain" include a domain having binding activity to the κ chain of an immunoglobulin, for example, an immunoglobulin binding domain of protein L, and a mutant thereof having immunoglobulin κ chain binding activity.

Examples of the immunoglobulin binding domain of protein L include B1 domain, B2 domain, B3 domain, B4 domain, and B5 domain of protein L produced by Finegoldia magna strain 312; and C1 domain, C2 domain, C3 domain, and C4 domain of protein L produced by F. magna strain 3316, and among these, C1 domain, C2 domain, C3 domain, and C4 domain are more preferred. B1 domain of protein L consists of an amino acid sequence set forth in SEQ ID NO:1. B2 domain of protein L consists of an amino acid sequence set forth in SEQ ID NO:2. B3 domain of protein L consists of an amino acid sequence set forth in SEQ ID NO:3. B4 domain of protein L consists of an amino acid sequence set forth in SEQ ID NO:4. B5 domain of protein L consists of an amino acid sequence set forth in SEQ ID NO:5. C1 domain of protein L consists of an amino acid sequence set forth in SEQ ID NO:6. C2 domain of protein L consists of an amino acid sequence set forth in SEQ ID NO:7. C3 domain of protein L consists of an amino acid sequence set forth in SEQ ID NO:8. C4 domain of protein L consists of an amino acid sequence set forth in SEQ ID NO:9. These immunoglobulin binding domains of protein L have high mutual similarity of amino acid sequences. Table 1 presents the alignment of the amino acid sequences of domains of protein L set forth in SEQ ID NO:1 to SEQ ID NO:9.

TABLE 1

| Domain | Seq ID. Nos | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|---|---|---|---|---|---|---|---|---|---|
| B1 | 1 | K | E | E | T | P | E | T | P | E | T | D | S | E | E | V | T | I | K | A |
| B2 | 2 | | | K | | | E | | | — | — | — | — | K | | | | | | |
| B3 | 3 | | | K | | | E | | | — | — | — | — | K | | | | | | |
| B4 | 4 | | | K | | | E | | | — | — | — | — | K | | | | | | |
| B5 | 5 | | — | K | V | D | K | | | — | — | E | K | | Q | | | | | E |
| C1 | 6 | | | — | | | — | | | — | — | — | | | | | | | | |
| C2 | 7 | | | K | — | | E | | | — | — | — | — | K | | | | | | V |
| C3 | 8 | | | — | | | | | | E | P | K | — | | | | | | | V |
| C4 | 9 | | | — | | | | | | E | P | K | — | | | | | | | V |

| Domain | 19 | 20 | 21 | 22 | 23 | 24 | 25 | 26 | 27 | 28 | 29 | 30 | 31 | 32 | 33 | 34 | 35 | 36 | 37 | 38 |
|---|---|---|---|---|---|---|---|---|---|---|---|---|---|---|---|---|---|---|---|---|
| B1 | N | L | I | F | A | N | G | S | T | Q | T | A | E | F | K | G | T | F | E | K |
| B2 | | | | Y | | D | | K | | | | | | | | | | | | E |
| B3 | | | | Y | | D | | K | | | | | | | | | | | | E |
| B4 | | | | Y | | D | | K | | | | | | | | | | | A | E |
| B5 | | I | Y | | E | D | | T | V | | | | | | T | | | | A | E |
| C1 | | | | | | D | | | | | N | | | | | | | A | | |
| C2 | | | | | | D | | K | | | | | | | | | | | | E |
| C3 | | | | | | D | | K | I | | | | | | | | | | | E |
| C4 | | | | | | D | | K | | | | | | | | | | | | E |

| Domain | Seq ID. Nos | 39 | 40 | 41 | 42 | 43 | 44 | 45 | 46 | 47 | 48 | 49 | 50 | 51 | 52 | 53 | 54 | 55 | 56 | 57 | 58 |
|---|---|---|---|---|---|---|---|---|---|---|---|---|---|---|---|---|---|---|---|---|---|
| B1 | 1 | A | T | S | E | A | Y | A | Y | A | D | T | L | K | K | D | N | G | E | Y | T |
| B2 | 2 | | | A | | | | R | | | | | A | | | | | | | | | |
| B3 | 3 | | | A | | | | R | | | | | L | | A | | E | | K | | | |
| B4 | 4 | | | A | | | | R | | | | | L | | A | | E | | K | | | |
| B5 | 5 | | | A | | | | R | | | | | L | | S | | E | H | K | | | |
| C1 | 6 | | V | | D | | | | | | | | A | | | | | | | | | |
| C2 | 7 | | | A | K | | | | | | | | L | | A | | E | | | | | |
| C3 | 8 | | | A | K | | | | | N | | | L | | A | | E | | | | | |
| C4 | 9 | | | A | | | | R | | | | | L | | A | | V | | | | | |

TABLE 1-continued

| Domain | 59 | 60 | 61 | 62 | 63 | 64 | 65 | 66 | 67 | 68 | 69 | 70 | 71 | 72 | 73 | 74 | 75 |
|---|---|---|---|---|---|---|---|---|---|---|---|---|---|---|---|---|---|
| B1 | V | D | V | A | D | K | G | Y | T | L | N | I | K | F | A | G | — |
| B2 | | | | | | | | | | | | | | | | | |
| B3 | | | | | | | | | | | | | | | | | |
| B4 | A | | L | E | | G | | | | I | | | R | | | | |
| B5 | A | | L | E | | G | | | | I | | | R | | | | |
| C1 | | | | | | | L | | | | | | | | | | K |
| C2 | A | | L | E | | G | N | | I | | | | | | | | |
| C3 | A | | L | E | | G | N | | I | | | | | | | | |
| C4 | A | | L | E | | G | | | I | | | | | | | | K |

In the table, a blank column means an amino acid residue that is the same as the amino acid residue at a position corresponding to the B1 domain. The symbol "–" means that the amino acid residue is not present.

An example of a mutant of the immunoglobulin binding domain of protein L may be a polypeptide consisting of an amino acid sequence having an identity of at least 85% with the sequence set forth in any one of SEQ ID NO:1 to SEQ ID NO:9, the polypeptide having immunoglobulin κ chain binding activity. Preferably, an example of a mutant of the immunoglobulin binding domain of protein L maybe a polypeptide consisting of an amino acid sequence having an identity of at least 85% with the sequence set forth in any one of SEQ ID NO:6 to SEQ ID NO:9, the polypeptide having immunoglobulin κ chain binding activity.

1. Immunoglobulin Binding Protein

The immunoglobulin binding protein of the present invention comprises at least one mutant of an immunoglobulin binding domain derived from an immunoglobulin binding domain of protein L (hereinafter, also referred to as mutant of the present invention). The mutant of the present invention can be obtained by introducing a predetermined mutation to a protein L-derived immunoglobulin binding domain, which is a parent domain, or a mutant thereof. The mutant of the present invention has immunoglobulin κ chain bindability, and the alkali tolerance is enhanced compared to the parent domain. The mutant immunoglobulin binding protein of the present invention having the mutant of the present invention can be used as a ligand of an affinity support.

Examples of the parent domain of the mutant of the present invention include protein L-derived immunoglobulin binding proteins, for example, C1 domain, C2 domain, C3 domain, C4 domain, B1 domain, B2 domain, B3 domain, B4 domain, B5 domain of protein L, and mutants thereof. Among these, C1 domain, C2 domain, C3 domain, C4 domain, and mutants thereof are preferred, and C4 domain and mutants thereof are more preferred.

The B1 to B5 domains and C1 to C4 domains of protein L, which can be used as the parent domain, are polypeptides consisting of amino acid sequences set forth in SEQ ID NO:1 to SEQ ID NO:9, respectively. Examples of the mutants of the B1 to B5 domains and C1 to C4 domains of protein L, which can be used as parent domains of the mutant of the present invention, comprise polypeptides consisting of amino acid sequences having an identity of at least 85% with the sequence set forth in any one of SEQ ID NO:1 to SEQ ID NO:9, the polypeptides having immunoglobulin κ chain binding activity.

A mutant of an immunoglobulin binding domain of protein L, which can be used as the parent domain, can be produced by subjecting an amino acid sequence of an immunoglobulin binding domain of protein L, to alterations such as insertion, deletion, substitution, or deletion of amino acid residues, and chemical modification of an amino acid residue. Examples of the means for insertion, deletion, substitution, or deletion of an amino acid residue include known means such as site-specific mutagenesis in a polynucleotide encoding the domain.

Therefore, preferred examples of the parent domain according to the present invention comprise polypeptides consisting of amino acid sequences set forth in SEQ ID NO:1 to SEQ ID NO:9, or amino acid sequences having an identity of at least 85% with the sequence having any one of SEQ ID NO:1 to SEQ ID NO:9, the polypeptides having immunoglobulin κ chain binding activity. More preferred examples of the parent domain comprise polypeptides consisting of an amino acid sequence set forth in any one of SEQ ID NO:6 to SEQ ID NO:9, or an amino acid sequence having an identity of at least 85% with the sequence set forth in any one of SEQ ID NO:6 to SEQ ID NO:9, the polypeptides having immunoglobulin κ chain binding activity. More preferred examples of the parent domain comprise polypeptides consisting of an amino acid sequence set forth in SEQ ID NO:9 or an amino acid sequence having an identity of at least 85% with the sequence set forth in SEQ ID NO:9, the polypeptides having immunoglobulin κ chain binding activity.

The mutant of the present invention that is contained in the immunoglobulin binding protein of the present invention is a polypeptide obtained by introducing at least one mutation selected from the group consisting of the following (a) to (h) into the amino acid sequence of the above-mentioned parent domain, the polypeptide retaining immunoglobulin κ chain binding activity:

(a) substitution with another amino acid residue or deletion of an amino acid residue at a position corresponding to the 17th-position of the amino acid sequence set forth in SEQ ID NO:9, or insertion of an amino acid residue into a position in front of or behind the relevant position;

(b) substitution with another amino acid residue or deletion of an amino acid residue at a position corresponding to the 26th-position of the amino acid sequence set forth in SEQ ID NO:9, or insertion of an amino acid residue into a position in front of or behind the relevant position;

(c) substitution with another amino acid residue or deletion of an amino acid residue at a position corresponding to the 35th-position of the amino acid sequence set forth in SEQ ID NO:9, or insertion of an amino acid residue into a position in front of or behind the relevant position;

(d) substitution with another amino acid residue or deletion of an amino acid residue at a position corresponding to the 42th-position of the amino acid sequence set forth in SEQ ID NO:9, or insertion of an amino acid residue into a position in front of or behind the relevant position;

(e) substitution with another amino acid residue or deletion of an amino acid residue at a position corresponding to the 44th-position of the amino acid sequence set forth in SEQ ID NO:9, or insertion of an amino acid residue into a position in front of or behind the relevant position;

(f) substitution with another amino acid residue or deletion of an amino acid residue at a position corresponding to the 54th-position of the amino acid sequence set forth in SEQ ID NO:9, or insertion of an amino acid residue into a position in front of or behind the relevant position;

(g) insertion of at least one amino acid residue between a position corresponding to the 54th-position and a position corresponding to the 55th-position of the amino acid sequence set forth in SEQ ID NO:9; and (h) deletion of at least one proline.

For example, the mutant of the present invention is produced by introducing at least one mutation selected from the group consisting of the above-described (a) to (h) into a polypeptide consisting of an amino acid sequence set forth in any one of SEQ ID NO:1 to SEQ ID NO:9. Alternatively, the mutant of the present invention is produced by introducing at least one mutation selected from the group consisting of the above-described (a) to (h) into a polypeptide of a protein L immunoglobulin binding domain mutant, which consists of an amino acid sequence having an identity of at least 85% with the sequence set forth in any one of SEQ ID NO:1 to SEQ ID NO:9, and the mutant has immunoglobulin κ chain binding activity. A mutant of the present invention thus produced has immunoglobulin κ chain binding activity and functions as an immunoglobulin binding domain. Furthermore, since the mutant of the present invention has enhanced alkali tolerance compared to the domain before mutation (parent domain), the mutant can be suitably used as an affinity ligand.

Preferably, the mutation of the above-described (a) is a substitution of an amino acid residue at a position corresponding to the 17th-position of the amino acid sequence set forth in SEQ ID NO:9 with another amino acid residue. This other amino acid residue is preferably Arg, Glu or Asp, and more preferably Arg. More preferably, the mutation of the (a) is a substitution of Lys at a position corresponding to the 17th-position of the amino acid sequence set forth in SEQ ID NO:9 with Arg.

Preferably, the mutation of the above-described (b) is a substitution of an amino acid residue at a position corresponding to the 26th-position of the amino acid sequence set forth in SEQ ID NO:9 with another amino acid residue. This other amino acid residue is preferably Arg, Glu or Asp, and more preferably Arg. More preferably, the mutation of the (b) is a substitution of Lys at a position corresponding to the 26th-position of the amino acid sequence set forth in SEQ ID NO:9 with Arg.

Preferably, the mutation of the above-described (c) is a substitution of an amino acid residue at a position corresponding to the 35th-position of the amino acid sequence set forth in SEQ ID NO:9 with another amino acid residue. This other amino acid residue is preferably Arg, Glu, or Asp, and more preferably Arg. More preferably, the mutation of the (c) is a substitution of Thr at a position corresponding to the 35th-position of the amino acid sequence set forth in SEQ ID NO:9 with Arg.

Preferably, the mutation of the above-described (d) is a substitution of an amino acid residue at a position corresponding to the 42th-position of the amino acid sequence set forth in SEQ ID NO:9 with another amino acid residue. This other amino acid residue is preferably Lys. More preferably, the mutation of the (d) is a substitution of Glu at a position corresponding to the 42th-position of the amino acid sequence set forth in SEQ ID NO:9 with Lys.

Preferably, the mutation of the above-described (e) is a substitution of an amino acid residue at a position corresponding to the 44th-position of the amino acid sequence set forth in SEQ ID NO:9 with another amino acid residue. This other amino acid residue is preferably Phe or Trp, and more preferably Phe. More preferably, the mutation of the (e) is a substitution of Thr at a position corresponding to the 44th-position of the amino acid sequence set forth in SEQ ID NO:9 with Phe.

Preferably, the mutation of the above-described (f) is a substitution of an amino acid residue at a position corresponding to the 54th-position of the amino acid sequence set forth in SEQ ID NO:9 with another amino acid residue. This other amino acid residue is preferably Gln. More preferably, the mutation of the (f) is a substitution of Asn at a position corresponding to the 54th-position of the amino acid sequence set forth in SEQ ID NO:9 with Gln.

Preferably, the mutation of the above-described (g) is an insertion of an amino acid residue at a position corresponding to the position between 54th-position and 55th-position of the amino acid sequence set forth in SEQ ID NO:9 of Ala, Leu or Tyr, and more preferably Ala or Tyr. Preferably, the mutation of the (g) is an insertion at a position between Asn at a position corresponding to the 54th-position and Gly at a position corresponding to the 55th-position of the amino acid sequence set forth in SEQ ID NO:9 of Ala, Leu or Try, and more preferably an insertion of Ala or Tyr.

Preferably, the mutation of the above-described (h) is deletion of at least one of Pro at a position corresponding to the 4th-position, 7th-position and 10th-position of the amino acid sequence set forth in SEQ ID NO:9, preferably, the deletion of Pro at all of these positions.

Suitable examples of combination of the mutations of the (a) to (h) comprise a combination of K26R, T35R and N54Q; a combination of K26R, T35R, E42K and N54Q; and a combination of K17R, K26R, T35R, E42K, N54Q, ΔP4, ΔP7 and ΔP10.

Regarding the means for mutating a parent domain, a method of introducing a mutation into a polynucleotide encoding the parent domain so that, for example, desired substitution, deletion, and insertion of amino acid residues occur, may be mentioned. Specific techniques for introducing a mutation into a polynucleotide include, for example, site-specific mutagenesis, homologous recombination, and SOE (splicing by overlap extension)-PCR (Gene, 1989, 77:61-68), and the detailed procedures of these are well known to those ordinarily skilled in the art.

An example of the mutant of the present invention obtainable by the above-described procedure may be a polypeptide consisting of an amino acid sequence having an identity of at least 85% with the sequence set forth in any one of SEQ ID NO:1 to SEQ ID NO:9 and having at least one mutation selected from the group consisting of the above-described (a) to (h), the polypeptide having immunoglobulin κ chain binding activity.

A preferred example of the mutant of the present invention may be a polypeptide consisting of an amino acid sequence having an identity of at least 85% with the sequence set forth in any one of SEQ ID NO:1 to SEQ ID NO:9, and having at least one of the following (a') to (h'):

(a') arginine, glutamic acid, or aspartic acid at a position corresponding to the 17th-position of the amino acid sequence set forth in SEQ ID NO:9;

(b') arginine, glutamic acid, or aspartic acid at a position corresponding to the 26th-position of the amino acid sequence set forth in SEQ ID NO:9;

(c') arginine, glutamic acid, or aspartic acid at a position corresponding to the 35th-position of the amino acid sequence set forth in SEQ ID NO:9;

(d') lysine at a position corresponding to the 42th-position of the amino acid sequence set forth in SEQ ID NO:9;

(e') phenylalanine or tryptophan at a position corresponding to the 44th-position of the amino acid sequence set forth in SEQ ID NO:9;

(f') glutamine at a position corresponding to the 54th-position of the amino acid sequence set forth in SEQ ID NO:9;

(g') alanine, leucine, or tyrosine between a position corresponding to the 54th-position and a position corresponding to the 55th-position of the amino acid sequence set forth in SEQ ID NO:9; and (h') deletion of proline at at least one position selected from the group consisting of a position corresponding to the 4th-position, a position corresponding to the 7th-position, and a position corresponding to the 10th-position of the amino acid sequence set forth in SEQ ID NO:9, and having immunoglobulin κ chain binding activity.

A more preferred example of the mutant of the present invention may be a polypeptide consisting of an amino acid sequence having an identity of at least 85% with the sequence set forth in any one of SEQ ID NO:1 to SEQ ID NO:9 and having at least any one of the following (a") to (q"):

(a") arginine at a position corresponding to the 17th-position of the amino acid sequence set forth in SEQ ID NO:9;

(b") arginine at a position corresponding to the 26th-position of the amino acid sequence set forth in SEQ ID NO:9;

(c") arginine at a position corresponding to the 35th-position of the amino acid sequence set forth in SEQ ID NO:9;

(d") lysine at a position corresponding to the 42th-position of the amino acid sequence set forth in SEQ ID NO:9;

(e") phenylalanine at a position corresponding to the 44th-position of the amino acid sequence set forth in SEQ ID NO:9;

(f") glutamine at a position corresponding to the 54th-position of the amino acid sequence set forth in SEQ ID NO:9;

($g_1$") alanine between a position corresponding to the 55th-position and a position corresponding to the 56th-position of the amino acid sequence set forth in SEQ ID NO:9;

($g_2$") tyrosine between a position corresponding to the 55th-position and a position corresponding to the 56th-position of the amino acid sequence set forth in SEQ ID NO:9;

($h_1$") deletion of proline at a position corresponding to the 4th-position of the amino acid sequence set forth in SEQ ID NO:9;

($h_2$") deletion of prolines at a position corresponding to the 4th-position and a position corresponding to the 7th-position of the amino acid sequence set forth in SEQ ID NO:9;

($h_3$") deletion of prolines at a position corresponding to the 4th-position, a position corresponding to the 7th-position, and a position corresponding to the 10th-position of the amino acid sequence set forth in SEQ ID NO:9;

(i") a combination of the (a") and (b");
(j") a combination of the (b"), (c"), and (f");
(k") a combination of the (b"), (c"), (d"), and (f"); and
(l") a combination of the (a"), (b"), (c"), (d"), (f"), and ($h_3$"), and having immunoglobulin κ chain binding activity.

An even more preferred example of the mutant of the present invention may be a polypeptide consisting of an amino acid sequence having an identity of at least 85% with the sequence set forth in any one of SEQ ID NO:1 to SEQ ID NO:9 and having any one of the (a"), (b"), (c"), (d"), (e"), (f"), (g1"), (g2"), (h1"), (h2") and (h3"); a combination of (a") and (b"); a combination of (b"), (c") and (f"); a combination of (b"), (c"), (d") and (f"); or a combination of (a"), (b"), (c"), (d"), (f") and (h3"), and having immunoglobulin κ chain binding activity.

A still more preferred example of the mutant of the present invention may be a polypeptide consisting of an amino acid sequence having an identity of at least 85% with the amino acid sequence set forth in SEQ ID NO:9 and having any one of the above-described (a") to (l"), the polypeptide having immunoglobulin κ chain binding activity. A still more preferred example of the mutant of the present invention may be a polypeptide consisting of an amino acid sequence set forth in any one of SEQ ID NO:10 to SEQ I NO:23.

It is desirable that the immunoglobulin binding protein of the present invention comprises one or more of the mutant of the present invention described above. Preferably, the immunoglobulin binding protein of the present invention comprises two or more, more preferably three or more, and even more preferably four or more, of the mutant of the present invention. On the other hand, the immunoglobulin binding protein of the present invention preferably comprises 12 or fewer, more preferably 8 or fewer, and even more preferably 7 or fewer, of the mutant of the present invention. For example, the immunoglobulin binding protein of the present invention preferably comprises 2 to 12, more preferably 3 to 8, and even more preferably 4 to 7, of the mutant of the present invention. In a case in which the immunoglobulin binding protein of the present invention comprises two or more of the mutant of the present invention, such a mutant maybe of the same kind or different kinds; however, it is preferable that the mutants are of the same kind.

The immunoglobulin binding protein of the present invention may comprise another immunoglobulin binding domain having binding activity to the immunoglobulin κ chain, in addition to the above-described mutant of the present invention. An example of this other domain may be an immunoglobulin binding domain of protein L, which does not have any of the mutations described in the above-mentioned (a) to (h), or a mutant of the domain.

A preferred example of the immunoglobulin binding protein of the present invention may be a polypeptide consisting of an amino acid sequence in which one kind or two or more kinds of amino acid sequences selected from SEQ ID NO:10 to SEQ ID NO:23 are linked into a straight chain comprising 2 to 12 sequences, more preferably 3 to 8 sequences, and even more preferably 4 to 7 sequences; and a more preferred example may be a polypeptide comprising any one amino acid sequence in which 2 to 12 sequences, more preferably 3 to 8 sequences, and even more preferably 4 to 7 sequences, of SEQ ID NO:10 to SEQ ID NO:23 are linked into a straight chain. However, preferred examples of the protein of the present invention are not limited to these.

2. Production of Immunoglobulin Binding Protein

The immunoglobulin binding protein of the present invention can be produced by a technique known in the pertinent art, for example, a chemical synthesis method based on the amino acid sequence or a recombination method. For example, the immunoglobulin binding protein of the present invention can be produced by utilizing known gene recombination technologies described in, for example, Current Protocols in Molecular Biology written by Frederick M. Ausbel et al., and Molecular Cloning edited by Sambrook et al. (Cold Spring Harbor Laboratory Press, 3rd edition, 2001). That is, by transforming an expression vector containing a polynucleotide encoding the immunoglobulin binding protein of the present invention in a host such as *Escherichia coli*, and culturing the recombinant thus obtained in an appropriate liquid medium, a target protein can be obtained economically efficiently in a large quantity from the cells after culturing. As a preferred expression vector, any known vector that can be replicated in a host cell can be used, and examples include the plasmids described in U.S. Pat. No. 5,151,350, and the plasmids described in Molecular Cloning (Cold Spring Harbor Laboratory Press, 3rd edition, 2001) edited by Sambrook, et al. Furthermore, the host for transformation is not particularly limited; however, any known host that is used for expressing a recombinant protein, such as a bacterium such as *Escherichia coli*; a fungus; an insect cell; or a mammalian cell, can be employed. In order to transform a host by introducing a nucleic acid into the host, any method that is known in the pertinent art may be used depending on the respective hosts, and for example, any known method described in Molecular Cloning edited by Sambrook et al. (Cold Spring Harbor Laboratory Press, 3rd edition, 2001) can be used. The methods for culturing a transformant (for example, cells of a bacterium) thus obtained and collecting a protein expressed therein are well known to those ordinarily skilled in the art. Alternatively, the immunoglobulin binding protein of the present invention may be expressed using a cell-free protein synthesis system.

Therefore, the present invention also provides a polynucleotide (for example, DNA) encoding the immunoglobulin binding protein of the present invention, a vector comprising the polynucleotide, and a transformant comprising the polynucleotide and the vector.

3. Affinity Support

The immunoglobulin binding protein of the present invention can be used as an affinity ligand. By immobilizing the immunoglobulin binding protein of the present invention on a solid-phase support, an affinity support having the immunoglobulin binding protein of the present invention as a ligand can be produced. The affinity support is a support having a protein L-derived immunoglobulin binding protein as a ligand, and has immunoglobulin κ chain binding activity. Furthermore, this affinity support has enhanced alkali tolerance compared to a support having wild type protein L or a domain thereof as a ligand.

The shape of the solid-phase support that is included in the affinity support of the present invention may be any arbitrary shape such as a particle, a membrane, a plate, a tube, a needle, or a fiber. This support maybe porous or non-porous. These supports can be used as packed beds or can be used in a suspension form. The suspension form comprises materials that are known as expanded beds and pure suspensions, and in this form, particles can be move freely. In the cases of a monolith, a packed bed, and an expanded bed, the procedure of separation generally follows a conventional chromatography method based on concentration gradient. In the case of a pure suspension, a batch method is used. Preferably, this support is a packing agent. Alternatively, the support may be in a form such as a chip, a capillary, or a filter.

According to an embodiment, this solid-phase support is such that the particle size is preferably from 20 μm to 200 μm. For example, in a case in which the support is a synthetic polymer, the particle size is preferably 20 μm or more, more preferably 30 μm or more, and preferably 100 μm or less, more preferably 80 μm or less, and for example, the particle size is preferably 20 to 100 μm, and more preferably 30 to 80 μm. For example, in a case in which the support is a polysaccharide, the particle size is preferably 50 μm or more, more preferably 60 μm or more, and preferably 200 μm or less, more preferably 150 μm or less, and for example, the particle size is preferably 50 to 200 μm, and more preferably 60 to 150 μm. When the particle size is less than 20 μm, the column pressure increases at a high flow rate, and the column cannot endure practical use. When the particle size is more than 200 μm, the amount of immunoglobulins binding with affinity supports (binding capacity) may be inferior. Meanwhile, the "particle size" according to the present specification is a volume average particle size obtainable by means of a laser diffraction scattering type particle size distribution analyzer, and more particularly, the particle size means a volume average particle size measured by a laser diffraction method according to ISO 13320 and JIS Z 8825-1. Specifically, the particle size refers to the average particle size that can be determined by measuring a volume-based particle size distribution by measuring the particle size distribution using a laser scattering diffraction type particle size distribution analyzer (for example, LS 13 320 (Beckman Coulter, Inc.)) and using Fluid R.I. Real 1.333, Sample R.I. Real 1.54, and Imaginary 0 as an optical model.

According to an embodiment, this solid-phase support is preferably porous and has a specific surface area of preferably 50 $m^2/g$ or more, more preferably 80 $m^2/g$ or more, and preferably 150 $m^2/g$ or less, more preferably 130 $m^2/g$ or less, and for example, the solid-phase support has a specific surface area of preferably 50 to 150 $m^2/g$ and more preferably 80 to 130 $m^2/g$. Here, when the specific surface area is less than 50 $m^2/g$, the binding capacity may be inferior, and when the specific surface area is more than 150 $m^2/g$, since the strength of the support is inferior, the support may be destroyed at a high flow rate, while the column pressure may increase. Meanwhile, the "specific surface area" according to the present specification is a value obtained by dividing the surface area of pores having a pore size of 10 to 5,000 nm, which is obtained using a mercury porosimeter, by the dry weight of the particles.

According to an embodiment, this solid-phase support is such that the volume average pore size is preferably from 100 nm to 1,400 nm. For example, in a case in which the support is a synthetic polymer, the volume average pore size is preferably 100 nm or more, more preferably 200 nm or more, and preferably 400 nm or less, more preferably 300 nm or less, and for example, the volume average pore size is preferably 100 to 400 nm, and more preferably 200 to 300 nm. For example, in a case in which the support is a polysaccharide, the volume average pore size is preferably 500 nm or more, more preferably 800 nm or more, and preferably 1,400 nm or less, more preferably 1,200 nm or less, and for example, the volume average pore size is preferably 500 to 1,400 nm, and more preferably 800 to 1,200 nm. Here, when the volume average pore size is less than 100 nm, a decrease in the binding capacity at a high flow rate may become noticeable, and when the volume average pore size is more than 1,400 nm, the binding capacity may be decreased regardless of the flow rate. Meanwhile, the "volume average pore size" according to the present specification is the volume average pore size of pores having a pore size of 10 to 5,000 nm, which is obtained using a mercury porosimeter.

In a case in which this solid-phase support satisfies the particle size, specific surface area, and pore size distribution of the ranges described above, the balance between the gaps between particles and relatively large pore diameters within the particles, which become flow channels for a solution as an object of purification, and the binding surface area of the molecules as an object of purification is optimized, and thus, the binding capacity at a high flow rate is maintained at a high level.

The material for this solid-phase support is, for example, a polymer having a hydrophilic surface, and for example, a polymer having a hydroxy group (—OH), a carboxy group (—COOH), an aminocarbonyl group (—CONH$_2$ or N-substituted type), an amino group (—NH$_2$ or substituted type), or an oligo- or polyethyleneoxy group on the outer surface (and if present, also on the inner surface) as a result of a hydrophilization treatment. According to an embodiment, the polymer may be a polymer obtained by subjecting a synthetic polymer such as polymethacrylate, polyacrylamide, polystyrene, or polyvinyl alcohol system to a hydrophilization treatment, and the polymer is preferably a polymer obtained by subjecting a synthetic polymer such as a polyfunctional (meth)acrylate or a copolymer crosslinked with a polyfunctional monomer to a hydrophilization treatment. Such a polymer is easily produced by a known method (for example, the method described in J. MATER. CHEM 1991, 1(3), 371-374 will be referred to). Alternatively, a commercially available product such as TOYOPEARL (Tosoh Corp.) is also used. The polymer according to another embodiment is a polysaccharide such as dextran, starch, cellulose, pullulan, or agarose. Such a polysaccharide is easily produced by a known method (for example, the method described in JP 4081143B2 will be referred to). Alternatively, a commercially available product such as SEPHAROSE (GE Healthcare Biosciences Corp.) can also be used. In other embodiments, an inorganic support such as silica or zirconium oxide is also acceptable.

According to an embodiment, one specific example of porous particles used as the solid-phase support maybe porous organic polymer particles containing a copolymer having, for example, 20% to 50% by mass of a crosslinkable vinyl monomer, 3 to 80% by mass of an epoxy group-containing vinyl monomer, and 20% to 80% by mass of a diol group-containing vinyl monomer, the porous organic polymer particles having a particle size of 20 to 80 μm, a specific surface area of 50 to 150 m$^2$/g, and a volume average pore size of 100 to 400 nm.

Meanwhile, the infiltration (pore volume) of pores having a pore size of 10 to 5,000 nm in a case in which the solid support is measured with a mercury porosimeter, is preferably from 1.3 mL/g to 7.0 mL/g. For example, in a case in which the support is a synthetic polymer, the pore volume is preferably 1.3 mL/g or more and preferably 7.0 mL/g or less, more preferably 5.0 mL/g or less, and even more preferably 2.5 mL/g or less, and for example, the pore volume is preferably 1.3 to 7.0 mL/g, more preferably 1.3 to 5.0 mL/g, and even more preferably 1.3 to 2.5 mL/g. Furthermore, for example, in a case in which the support is a polysaccharide, the pore volume is preferably 3.0 to 6.0 mL/g.

The method for binding a ligand (that is, the immunoglobulin binding protein of the present invention) to the solid-phase support, can be carried out using a general method of immobilizing a protein on a support. Examples include a method of using a support having a carboxy group, activating this carboxy group by means of N-hydroxysuccinic acid imide, and reacting the carboxy group with an amino group of a ligand; a method of using a support having an amino group or a carboxy group, reacting the support with a carboxy group or an amino group of a ligand in the presence of a dehydration condensing agent such as a water-soluble carbodiimide, and thereby forming an amide bond; a method of using a support having a hydroxyl group, activating the support with a cyan halide such as cyan bromide, and reacting the support with an amino group of a ligand; a method of tosylating or tresylating a hydroxyl group of a support, and reacting the hydroxyl group with an amino group of a ligand; a method of introducing an epoxy group into a support by means of, for example, bisepoxide or epichlorohydrin, and reacting the support with an amino group, a hydroxyl group, or a thiol group of a ligand; and a method of using a support having an epoxy group, and reacting the support with an amino group, a hydroxy group, or a thiol group of a ligand. Among the methods described above, from the viewpoint of the stability in an aqueous solution to be subjected to a reaction, a method of binding a ligand via an epoxy group is desirable.

A hydroxyl group, which is a ring-opening epoxy group produced by ring-opening of an epoxy group, hydrophilizes a support surface and prevents non-specific adsorption of a protein for example, also enhances the toughness of a support in water, and thus accomplishes the role of preventing the destruction of the support at a high flow rate. Therefore, in a case in which residual epoxy groups that are not bound to the ligand exist in the support after having the ligand immobilized thereon, it is preferable to ring-open these residual epoxy groups. Regarding the method of ring-opening epoxy groups in the support, for example, a method of stirring the support with an acid or an alkali under heating or at room temperature in an aqueous solvent may be mentioned. Furthermore, epoxy groups may also be ring-opened with a blocking agent having a mercapto group, such as mercaptoethanol or thioglycerol, or with a blocking agent having an amino group, such as monoethanolamine. A more preferred ring-opened epoxy group is a ring-opened epoxy group obtainable by ring-opening an epoxy group contained in the support by means of thioglycerol. Thioglycerol has low toxicity even compared to, for example, mercaptoethanol as a raw material, and an epoxy ring-opened group having thioglycerol added thereto has an advantage that the non-specific adsorption occurs at a lower level than a ring-opened group obtained by a blocking agent having an amino group and that the dynamic binding amount is high.

If necessary, a molecule having an arbitrary length (spacer) may be introduced between a solid-phase support and a ligand. Examples of the spacer include a polymethylene chain, a polyethylene glycol chain, and saccharides.

Since the affinity support of the present invention has a ligand showing improved alkali-resistant, its high static binding capacity (SBC) can be maintained even after repeated alkali-cleansing. Furthermore, since the affinity support of the present invention uses a ligand having immunoglobulin κ chain binding activity, the affinity support can be used for the purification of immunoglobulins such as IgG, IgM, IgA, IgD, and IgE, as well as low molecular weight antibodies such as Fab and a single-chain antibody (scFv).

4. Method for Isolating Antibody or Fragment Thereof

A method for isolating an antibody or a fragment thereof (hereinafter, simply described as antibody) according to an embodiment of the present invention will be explained. The method for isolating an antibody according to the present embodiment suitably comprises a step (first step) of passing a sample containing an antibody through an affinity support having the immunoglobulin binding protein of the present invention immobilized thereon, and adsorbing the antibody to the support; and a step (second step) of eluting the antibody from the support.

In the first step, a sample containing an antibody is allowed to flow through a column packed with the affinity support of the present invention under the conditions in which the antibody adsorbs to the ligand (immunoglobulin binding protein of the present invention). In this first step, most of the substances other than the antibody in the sample pass through the column without being adsorbed to the ligand. Thereafter, if necessary, the support may be washed with a neutral buffer solution comprising a salt such as NaCl, in order to remove a portion of substances weakly retained by the ligand.

In the second step, an appropriate buffer solution at pH 2 to 5 is allowed to flow, and the antibody adsorbed to the ligand is eluted. By collecting this eluate, the antibody can be isolated from the sample.

According to an embodiment of the method for isolating an antibody of the present invention, an antibody that has been isolated is used as an antibody drug. Therefore, according to an embodiment, the present invention provides a method for producing an antibody drug using the affinity support of the present invention. The procedure of the method is basically similar to the procedure of the method for isolating an antibody described above, except that a sample containing an intended antibody drug is used.

EXAMPLES

Hereinafter, the present invention will be described more specifically by way of Examples. Furthermore, the following description discloses embodiments of the present invention in a general manner, and unless particularly stated otherwise, the present invention is not intended to be limited by such description.

Reference Example 1

Synthesis of Porous Particles (1) 8.2 g of glycidyl methacrylate (manufactured by Mitsubishi Rayon Co., Ltd.), 65.9 g of trimethylolpropane trimethacrylate (manufactured by Sartomer USA, LLC), and 90.6 g of glycerin monomethacrylate (manufactured by NOF Corp.) were dissolved in 245.8 g of 2-octanone (manufactured by Toyo Gosei Co., Ltd.) and 62 g of acetophenone (manufactured by Wako Pure Chemical Industries, Ltd.), 2 g of 2,2'-azoisobutyronitrile (manufactured by Wako Pure Chemical Industries, Ltd.) was added thereto, and thus an organic monomer solution was prepared.

(2) To 4,240 g of pure water, 8.5 g of polyvinyl alcohol (PVA-217 manufactured by Kuraray Co., Ltd.), 0.43 g of sodium dodecyl sulfate (EMAL 10G manufactured by Kao Corp.), and 21.3 g of sodium sulfate (manufactured by Wako Pure Chemical Industries, Ltd.) were added, the mixture was stirred overnight, and thus an aqueous solution was prepared.

(3) The aqueous solution obtained in (2) was introduced into a 7-L separable flask, the flask was equipped with a thermometer, a stirring blade, and a cooling tube and placed in a warm water bath, and the aqueous solution was stirred at 600 rpm in a nitrogen atmosphere. Subsequently, the separable flask was warmed by the warm water bath, and when the temperature of the aqueous solution reached 85° C., the organic monomer solution obtained in (1) was added to this aqueous solution using a dropping funnel. Stirring was carried out for 5 hours.

(4) The reaction liquid obtained in (3) was transferred into a 5-L bottle made of polypropylene, the reaction liquid was left to stand still until particles were suspended, and excess water was suctioned from the lower part and discarded. Acetone was added to the liquid comprising the remaining particles to precipitate the particles, the system was left to stand still for 3 minutes, and then acetone was removed by decantation. This operation was repeated twice. The particles were precipitated by adding water thereto, subsequently the system was left to stand still for 3 minutes, and decantation was performed. This operation was repeated twice to wash the particles, subsequently the liquid portion was substituted with acetone, and the particles were dried in air overnight and then dried in a vacuum dryer. Thus, 90 g of porous particles (hereinafter, described as PB) were obtained. The average particle size of the PB was 53 µm, and the specific surface area was 95 $m^2/g$.

Example 1

Production of Immunoglobulin κ0 Chain Binding Proteins (KBP1 to KBP14)

Plasmids in which each of genes encoding the proteins comprising a plurality of immunoglobulin binding domain mutants (mutated domains) each consisting of an amino acid sequence set forth in any one of SEQ ID NO:10 to SEQ ID NO:23 had been inserted into pET-24a(+) vector, were purchased from an artificial gene synthesis manufacturer. *Escherichia coli* competent cells BL21 (DE3) (manufactured by New England Biolabs, Ltd.) were transformed with each of these plasmids, and thus transformed cells were obtained.

The transformed cells thus obtained were incubated at 37° C. until the absorbance (OD600) reached about 10. Subsequently, IPTG (manufactured by Sigma-Aldrich Corp.) was added thereto so as to obtain a final concentration of 1 mM, the culture was incubated for 4 hours at 37° C., and thereby a recombinant type immunoglobulin κ chain binding protein was expressed. The cells were collected and disrupted in a Tris buffer solution at pH 9.5. From the disrupted cell suspension thus obtained, the recombinant immunoglobulin binding protein was purified by anion exchange chromatography (Q-SEPHAROSE FF, manufactured by GE Healthcare Biosciences Corp.) and cation exchange chromatography (SP-SEPHAROSE FF, manufactured by GE Healthcare Biosciences Corp.). The immunoglobulin binding protein thus purified was dialyzed for 16 hours against a 10 mM citric acid buffer solution at pH 6.6. The purity of the recombinant type immunoglobulin binding proteins checked by SDS-PAGE was 95% or higher. The recombinant immunoglobulin κ chain binding proteins thus purified were designated as KBP1 to KBP14, respectively.

Comparative Example 1

Production of Immunoglobulin κ Chain Binding Protein (KBP0)

Recombinant type immunoglobulin κ chain binding protein KBP0 was produced by a procedure similar to Example 1 using a plasmid in which a gene encoding a protein that comprises a plurality of wild type immunoglobulin binding domains each consisting of an amino acid sequence set forth in SEQ ID NO:9 had been inserted.

The structures of the immunoglobulin κ chain binding proteins (KBP0 to KBP14) produced in Example 1 and Comparative Example 1 are presented in Table 2.

TABLE 2

| Name | Mutated domain sequence | Parent domain | Introduced mutation | Number of domains |
|---|---|---|---|---|
| KBP0 | — | C4 (SEQ ID NO: 9) | — | 4 |
| KBP1 | SEQ ID NO: 10 | | K17R | 4 |
| KBP2 | SEQ ID NO: 11 | | K26R | 4 |
| KBP3 | SEQ ID NO: 12 | | T35R | 4 |
| KBP4 | SEQ ID NO: 13 | | Y44F | 4 |
| KBP5 | SEQ ID NO: 14 | | N54Q | 4 |
| KBP6 | SEQ ID NO: 15 | | A is inserted between N54G55 | 4 |
| KBP7 | SEQ ID NO: 16 | | Y is inserted between N54G55 | 4 |
| KBP8 | SEQ ID NO: 17 | | ⊿ P4 | 4 |
| KBP9 | SEQ ID NO: 18 | | ⊿ P4,⊿ P7 | 4 |
| KBP10 | SEQ ID NO: 19 | | ⊿ P4,⊿ P7,⊿ P10 | 4 |
| KBP11 | SEQ ID NO: 20 | | K17R, K26R | 4 |
| KBP12 | SEQ ID NO: 21 | | K26R, T35R, N54Q | 4 |
| KBP13 | SEQ ID NO: 22 | | K26R, T35R, E42K, N54Q | 4 |
| KBP14 | SEQ ID NO: 23 | | ⊿ P4,⊿ P7,⊿ P10, K17R, K26R, T35R, E42K, N54Q | 4 |

Example 2

Preparation of Ligand Protein-Immobilized Porous Particles

The PB prepared in Example 1 was suspended in 150 µL of pure water so that the 8 mg of the PB would be contained, the suspension was transferred into a filter tube (Millipore Corp.) and centrifuged, and thereby pure water was removed. To this, 450 µL of a 0.1 M carbonate buffer solution (pH 10) comprising 0.85 M sodium sulfate, in which 1 mg of KBP0 prepared in Comparative Example 1 was dissolved, was added, and the mixture was shaken for 5 hours at 25° C. so as to bind KBP0 to PB. The particles thus produced were filtered and then mixed with 400 µL of 1 M thioglycerol, and the mixture was allowed to react for 16 hours at 25° C. Residual epoxy groups were blocked, the mixture was washed with 30 mM NaOH and then washed with a 50 mM sodium citrate buffer (pH 2.5) and a 0.1 M sodium phosphate buffer (pH 7.6), and 400 µL of bound porous particles (KBP0/PB) were obtained.

By a similar procedure, porous particles having any one of KBP1 to KBP14 bound thereto (KBP1/PB to KBP14/PB) were obtained.

Test Example 1

Measurement of Static Binding Capacity (SBC)

(1) Measurement of SBC of Porous Particles Without Alkali Treatment

100 µL of a suspension comprising 2 mg of porous particles (KBP0/PB) was transferred into a filter tube (Millipore Corp.) and centrifuged, and a permeate was removed. To this, 400 µL of a 20 mM phosphate buffer (pH 7.5) was added, the mixture was centrifuged, a permeate was removed, and the particles in the tube were equilibrated. Next, to this, 400 µL of a 20 mM phosphate buffer (pH 7.5) comprising 0.8 mg of Fab was added, and the mixture was incubated for one hour and centrifuged. Subsequently, the residue was further washed with 400 µL of a 20 mM phosphate buffer (pH 7.5) and centrifuged. Next, 400 µL of a 50 mM sodium citrate buffer (pH 2.5) was added thereto, the mixture was centrifuged, and an eluate comprising Fab was collected. The amount of Fab in the eluate was calculated by measuring the absorbance, and the static binding capacity (SBC) was determined from the amount of eluted Fab and the support volume. By a similar procedure, the SBC values of KBP1/PB to KBP14/PB were determined.

(2) Measurement of SBC Of Alkali-Treated Porous Particles

100 µL of a suspension comprising 2 mg of porous particles (KBP0/PB) was transferred into a filter tube (Millipore Corp.) and centrifuged, and a permeate was removed. To this, 400 µL of a 0.1 M NaOH was added, the mixture was immersed while being shaken for 24 hours, subsequently the mixture was centrifuged, and a permeate was removed. Subsequently, 400 µL of a 20 mM phosphate buffer (pH·BR>V.5) was added, the mixture was centrifuged, and a permeate was removed. Thus, the particles in the tube were equilibrated. To this, 400 µL of a 20 mM phosphate buffer (pH 7.5) comprising 0.8 mg of Fab was added, and the mixture was incubated for one hour and centrifuged. Subsequently, the residue was further washed with 400 µL of a 20 mM phosphate buffer (pH 7.5) and centrifuged. Next, 400 µL of a 50 mM sodium citrate buffer (pH 2.5) was added thereto, the mixture was centrifuged, and an eluate comprising Fab was collected. The amount of Fab in the eluate was calculated by measuring the absorbance, the static binding capacity (SBC) was determined from the amount of eluted Fab and the support volume, and a relative value with respect to the SBC without alkali treatment (SBC retention ratio, %) was calculated. By a similar procedure, the SBC retention ratios (%) of KBP1/PB to KBP14/PB were determined.

(3) Results

The measurement results are presented in Table 3. Under the conditions in which an alkali treatment was not performed, the SBC values of the porous particles (KBP1/PB to KBP14/PB) that used mutated domains were almost equal to that of KBP0/PB that used a wild type domain. On the other hand, after an alkali treatment, the SBC values of KBP1/PB to KBP14/PB were markedly increased compared to KBP0/PB. From these results, it was found that ligand proteins KBP1 to KBP14 comprising mutated domains have high alkali tolerance compared to a wild type protein, and can maintain high antibody binding properties even under severe conditions of being exposed to 0.1 M sodium hydroxide for 24 hours.

TABLE 3

| Porous particles | SBC without alkali treatment (mg/mL-particles) | SBC retention ratio (%) after alkali treatment |
|---|---|---|
| KBP0/PB | 60 | 39 |
| KBP1/PB | 56 | 46 |
| KBP2/PB | 59 | 46 |
| KBP3/PB | 58 | 48 |
| KBP4/PB | 47 | 49 |
| KBP5/PB | 63 | 51 |
| KBP6/PB | 61 | 58 |
| KBP7/PB | 64 | 73 |
| KBP8/PB | 60 | 45 |
| KBP9/PB | 60 | 42 |
| KBP10/PB | 61 | 49 |
| KBP11/PB | 56 | 47 |
| KBP12/PB | 65 | 71 |
| KBP13/PB | 64 | 72 |
| KBP14/PB | 65 | 80 |

The invention claimed is:

1. An immunoglobulin binding protein, comprising at least one mutant of an immunoglobulin binding domain, wherein the at least one mutant of the immunoglobulin binding domain consists of an amino acid sequence having an identity of at least 95% with the sequence set forth in SEQ ID NO:9, the amino acid sequence having a substitution of lysine at a position corresponding to the 26th-position of the amino acid sequence set forth in SEQ ID NO:9 with arginine, and at least one of a substitution of threonine at a position corresponding to the 35th-position of the amino acid sequence set forth in SEQ ID NO:9 with arginine, a substitution of asparagine at a position corresponding to the 54th-position of the amino acid sequence set forth in SEQ ID NO:9 with glutamine, and a substitution of glutamic acid at a position corresponding to the 42nd-position of the amino acid sequence set forth in SEQ ID NO:9 with lysine, and wherein the mutant has immunoglobulin κ chain binding activity.

2. The immunoglobulin binding protein according to claim 1, wherein the at least one mutant has the substitution of lysine at a position corresponding to the 26th-position of the amino acid sequence set forth in SEQ ID NO:9 with arginine, and the substitution of threonine at a position corresponding to the 35th-position of the amino acid sequence set forth in SEQ ID NO:9 with arginine.

3. The immunoglobulin binding protein according to claim 1, wherein the at least one mutant has the substitution of lysine at a position corresponding to the 26th-position of the amino acid sequence set forth in SEQ ID NO:9 with arginine and the substitution of asparagine at a position corresponding to the 54th-position of the amino acid sequence set forth in SEQ ID NO:9 with glutamine.

4. The immunoglobulin binding protein according to claim 1, wherein the at least one mutant has the substitution of lysine at a position corresponding to the 26th-position of the amino acid sequence set forth in SEQ ID NO:9 with arginine and the substitution of glutamic acid at a position corresponding to the 42nd-position of the amino acid sequence set forth in SEQ ID NO:9 with lysine.

5. The immunoglobulin binding protein according to claim 1, wherein the at least one mutant has the substitution of lysine at a position corresponding to the 26th-position of the amino acid sequence set forth in SEQ ID NO:9 with arginine, the substitution of threonine at a position corresponding to the 35th-position of the amino acid sequence set forth in SEQ ID NO:9 with arginine, the substitution of asparagine at a position corresponding to the 54th-position of the amino acid sequence set forth in SEQ ID NO:9 with glutamine, and the substitution of glutamic acid at a position corresponding to the 42th-position of the amino acid sequence set forth in SEQ ID NO:9 with lysine.

6. A polynucleotide encoding the immunoglobulin binding protein according to claim 1.

7. A vector comprising the polynucleotide according to claim 6.

8. A transformant comprising the vector according to claim 7.

9. An affinity support, comprising a solid-phase support; and the immunoglobulin binding protein according to claim 1 bound to the solid-phase support.

10. A method, comprising:
    isolating an antibody or a fragment thereof with the affinity support according to claim 9.

11. A method for producing an immunoglobulin binding protein, the method comprising:
    (i) expressing the immunoglobulin binding protein according to claim 1 in a transformant comprising a vector comprising a polynucleotide encoding the immunoglobulin binding protein or in a cell-free protein synthesis system, or
    (ii) chemically synthesizing the immunoglobulin binding protein according to claim 1.

12. A method for producing a mutant of an immunoglobulin binding domain, the method comprising:
    introducing a mutation to a polypeptide consisting of an amino acid sequence set forth in SEQ ID NO:9 or an amino acid sequence having an identity of at least 95% therewith, the polypeptide having immunoglobulin κ chain binding activity:
    wherein the mutation is a substitution of lysine at a position corresponding to the 26th-position of the amino acid sequence set forth in SEQ ID NO:9 with arginine, and
    at least one of a substitution of threonine at a position corresponding to the 35th-position of the amino acid sequence set forth in SEQ ID NO:9 with arginine, a substitution of asparagine at a position corresponding to the 54th-position of the amino acid sequence set forth in SEQ ID NO:9 with glutamine, and a substitution of glutamic acid at a position corresponding to the 42nd-position of the amino acid sequence set forth in SEQ ID NO:9 with lysine.

13. method for producing an affinity support, the method comprising:
    immobilizing the immunoglobulin binding protein according to claim 1 on a solid-phase support.

* * * * *

UNITED STATES PATENT AND TRADEMARK OFFICE
CERTIFICATE OF CORRECTION

| | |
|---|---|
| PATENT NO. | : 11,753,449 B2 |
| APPLICATION NO. | : 16/649879 |
| DATED | : September 12, 2023 |
| INVENTOR(S) | : Jun-ichi Yasuoka et al. |

It is certified that error appears in the above-identified patent and that said Letters Patent is hereby corrected as shown below:

In the Claims

Column 44, Line 35, Claim 13, "method for producing", should read -- A method for producing --.

Signed and Sealed this
Twenty-seventh Day of February, 2024

Katherine Kelly Vidal
*Director of the United States Patent and Trademark Office*